United States Patent
Sato et al.

(10) Patent No.: US 6,740,772 B1
(45) Date of Patent: May 25, 2004

(54) PROSTAGLANDIN DERIVATIVES

(75) Inventors: Fumie Sato, Kanagawa (JP); Tohru Tanami, Tokyo (JP); Hideo Tanaka, Tokyo (JP); Naoya Ono, Tokyo (JP); Makoto Yagi, Tokyo (JP); Hitomi Hirano, Tokyo (JP)

(73) Assignees: Taisho Pharmaceutical Co., Ltd., Tokyo (JP); Fumie Sato, Kanagawa (JP)

( * ) Notice: Subject to any disclaimer, the term of this patent is extended or adjusted under 35 U.S.C. 154(b) by 103 days.

(21) Appl. No.: 10/070,643

(22) PCT Filed: Sep. 8, 2000

(86) PCT No.: PCT/JP00/06162
§ 371 (c)(1),
(2), (4) Date: Mar. 11, 2002

(87) PCT Pub. No.: WO01/19790
PCT Pub. Date: Mar. 22, 2001

(30) Foreign Application Priority Data

Sep. 10, 1999 (JP) .............................. 11-256727
Nov. 15, 1999 (JP) .......................... 11-323804
Jun. 23, 2000 (JP) ........................ 2000-189121

(51) Int. Cl.[7] ............................................. C07C 177/00
(52) U.S. Cl. ...................... 560/121; 562/503; 514/530
(58) Field of Search ..................... 560/121; 562/503; 514/530

(56) References Cited

U.S. PATENT DOCUMENTS

| | | | |
|---|---|---|---|
| 4,029,681 A | 6/1977 | Smith | |
| 5,545,666 A | 8/1996 | Sato et al. | |
| 5,756,818 A | 5/1998 | Buchmann et al. | |
| 5,891,910 A | 4/1999 | Buchmann et al. | |
| 6,225,347 B1 | 5/2001 | Buchmann et al. | |

FOREIGN PATENT DOCUMENTS

| | | |
|---|---|---|
| AU | 88726/91 | 6/1992 |
| EP | 0 510 154 B1 | 5/1995 |
| JP | 52-100446 | 8/1977 |
| JP | 2-502009 | 7/1990 |
| JP | 7-285929 | 10/1995 |
| WO | WO 94/08959 | 4/1994 |
| WO | WO 95/06634 | 3/1995 |
| WO | WO 95/18101 | 7/1995 |

Primary Examiner—Paul J. Killos
(74) Attorney, Agent, or Firm—Sughrue Mion, PLLC

(57) ABSTRACT

A prostaglandin derivative represented by the formula:

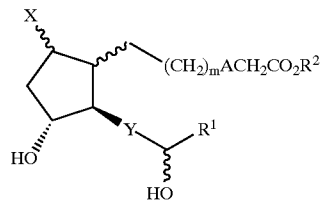

wherein X is a halogen atom in the α- or β-position, Y is an ethylene group, a vinylene group or an ethynylene group, A is a group represented by the formula: $O(CH_2)_n$, $S(O)_p(CH_2)_n$, $O(CH_2)_qO(CH_2)_r$, $O(CH_2)_qS(O)_p(CH_2)_r$, $S(O)_p(CH_2)_qS(O)_p(CH_2)_r$ or $S(O)_p(CH_2)_qO(CH_2)_r$ (wherein n is an integer of 1 to 5, p is 0, 1 or 2, q is an integer of 1 to 3, and r is 0 or 1), $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a $C_{5-10}$ alkyl group, a $C_{5-10}$ alkenyl group, a $C_{5-10}$ alkynyl group or a bridged cyclic hydrocarbon group, $R^2$ is a hydrogen atom, a $C_{1-10}$ alkyl group or a $C_{3-10}$ cycloalkyl group, and m is 0, 1 or 2], a pharmaceutically acceptable salt thereof or a hydrate thereof.

The present invention is to provide novel PG derivatives having an excellent $PGD_2$-like agonistic activity and a sleep-inducing action.

8 Claims, No Drawings

PROSTAGLANDIN DERIVATIVES

TECHNICAL FIELD

The present invention relates to novel prostaglandin derivatives, pharmaceutically acceptable salts thereof and hydrates thereof.

BACKGROUND ART

Since prostaglandin (PG) exhibits various important physiological actions in a trace amount, the biological activities of a great number of natural PGs and synthesized PG derivatives have been investigated with the intention of a practical use as medicines and have been reported in many literatures and patents. Among them, Japanese Patent Kohyo Hei 2-502009 discloses a group of PG derivatives substituted with a halogen atom at the 9-position. Furthermore, PG derivatives having a $PGD_2$-like agonistic activity are reported by K-H Thierauch et al., in Drug of the Future, vol. 17, page 809 (1992).

In addition, PGs have been not only reported on their various central nervous actions and but also clarified as to the intracerebral content, biosynthesis, metabolic pathway, their intracerebral localization and changes with growth or aging, and there has been taken an interest in the relation between sleep and wake by PGs. Among them, $PGD_2$ has been known as an intracerebral humoral factor which controls the occurrence or maintenance of sleep, and it was made clear that the sleep induced by $PGD_2$ in monkeys is undistinguished from their spontaneous natural sleep in brain wave or behavior (Proc. Natl. Acad. Sci. USA, vol. 85, pp. 4082–4086 (1988)), therefore this compound was expected as a new compound having a sleep-inducing action.

However, $PGD_2$ derivatives including $PGD_2$ are presently unpractical due to the problems concerning their intracerebral transition and stability. Furthermore, there has not been specifically reported about sleep-inducing action of PG derivatives other than $PGD_2$ derivatives.

An object of the present invention is to provide novel PG derivatives having a $PGD_2$-like agonistic activity and a sleep-inducing action.

DISCLOSURE OF THE INVENTION

As a result of the continued extensive studies, the present inventors have found that novel prostaglandin derivatives represented by the following Formula (I) achieve the above-objects, and thereby the present invention has been accomplished.

That is, the present invention is directed to a prostaglandin derivative represented by Formula (I):

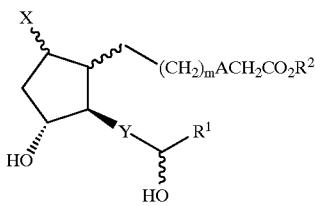

(I)

[wherein X is a halogen atom in the α- or β-position, Y is an ethylene group, a vinylene group or an ethynylene group, A is a group represented by the formula: $O(CH_2)_n$,
$S(O)_p(CH_2)_n$,
$O(CH_2)_qO(CH_2)_r$,
$O(CH_2)_qS(O)_p(CH_2)_r$,
$S(O)_p(CH_2)_qS(O)_p(CH_2)_r$ or
$S(O)_p(CH_2)_qO(CH_2)_r$
(wherein n is an integer of 1 to 5, p is 0, 1 or 2, q is an integer of 1 to 3, and r is 0 or 1), $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a $C_{5-10}$ alkyl group, a $C_{5-10}$ alkenyl group, a $C_{5-10}$ alkynyl group or a bridged cyclic hydrocarbon group, $R^2$ is a hydrogen atom, a $C_{1-10}$ alkyl group or a $C_{3-10}$ cycloalkyl group, and m is 0, 1 or 2], a pharmaceutically acceptable salt thereof or a hydrate thereof.

Furthermore, the present invention is directed to a pharmaceutical preparation which comprises as an effective Ingredient the compound represented by formula (I), the pharmaceutically acceptable salt thereof or the hydrate thereof.

In the present invention, the vinylene group refers to a cis- or a trans-vinylene group. The halogen atom refers to a fluorine atom, a chlorine atom, a bromine atom or an iodine atom.

The $C_{3-10}$ cycloalkyl group means a cycloalkyl group having 3 to 10 carbon atoms, examples of which are a cyclopropyl group, a cyclobutyl group, a cyclopentyl group, a cyclohexyl group and a cycloheptyl group.

The $C_{1-4}$ alkyl-$C_{3-10}$ cycloalkyl group means a cycloalkyl group having 3 to 10 carbon atoms substituted with a straight or branched alkyl group having 1 to 4 carbon atoms, examples of which are a methylcyclopropyl group, a methylcyclohexyl group and an ethylcyclohexyl group.

The $C_{3-10}$ cycloalkyl-$C_{1-4}$ alkyl group means a straight or branched alkyl group having 1 to 4 carbon atoms substituted with a cycloalkyl group having 3 to 10 carbon atoms, examples of which are a cyclopropylmethyl group, a cyclobutylmethyl group, a cyclopentylmethyl group, a cyclopentylethyl group, a cyclohexylmethyl group, a cyclohexylethyl group and a cycloheptylmethyl group.

The $C_{5-10}$ alkyl group means a straight or branched alkyl group having 5 to 10 carbon atoms, and examples of which are a pentyl group, a hexyl group, a heptyl group, an octyl group, a 1-methylpentyl group, a 2-methylpentyl group, a 1-methylhexyl group, a 2-methylhexyl group, a 2,4-dimethylpentyl group, a 2-ethylpentyl group, a 2-methylheptyl group, a 2-ethylhexyl group, a 2-propylpentyl group, a 2-propylhexyl group and a 2,6-dimethylheptyl group.

The $C_{5-10}$ alkenyl group means a straight or branched alkenyl group having 5 to 10 carbon atoms, examples of which are a 3-pentenyl group, a 4-hexenyl group, a 5-heptenyl group, a 4-methyl-3-pentenyl group, a 2,4-dimethylpentenyl group, a 6-methyl-5-heptenyl group and a 2,6-dimethyl-5-heptenyl group.

The $C_{5-10}$ alkynyl group means a straight or branched alkynyl group having 5 to 10 carbon atoms, examples of which are a 3-pentynyl group, a 3-hexynyl group, a 4-hexynyl group, a 1-methylpent-3-ynyl group, a 2-methylpent-3-ynyl group, a 1-methylhex-3-ynyl group and a 2-methylhex-3-ynyl group.

Examples of the bridged cyclic hydrocarbon group are a bornyl group, a norbornyl group, an adamantyl group, a pinanyl group, a thujyl group, a caryl group and a camphanyl group.

The $C_{1-10}$ alkyl group means a straight or branched alkyl group having 1 to 10 carbon atoms, examples of which are a methyl group, an ethyl group, a propyl group, an isopropyl group, a butyl group, an isobutyl group, a tert-butyl group, a pentyl group, an isopentyl group, a 2-ethylpropyl group, a hexyl group, an isohexyl group, a 1-ethylbutyl group, a heptyl group, an isoheptyl group, an octyl group, an nonyl group and a decyl group.

Examples of the pharmaceutically acceptable salt are salts with alkali metals (e.g., sodium or potassium), alkali earth metals (e.g., calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium and tris(hydroxymethyl)aminomethane.

Preferable compounds of the present invention are those of Formula (I) wherein $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a branched $C_{5-10}$ alkyl group, a branched $C_{5-10}$ alkenyl group, a branched $C_{5-10}$ alkynyl group or a bridged cyclic hydrocarbon group. Further preferable compounds of the present invention are those of Formula (I) wherein X is a chlorine or bromine atom in the α- or β-position, $R^1$ is a $C_{3-10}$ cycloalkyl group, a $C_{3-10}$ cycloalkyl-$C_{1-4}$ alkyl group or a branched $C_{5-10}$ alkenyl group, and $R^2$ is a hydrogen atom or a $C_{1-10}$ alkyl group.

Furthermore, Y is preferably a vinylene group or an ethynylene group, and more preferably an ethynylene group. A is preferably a group represented by the formula: $S(O)_p(CH_2)_n$, $S(O)_p(CH_2)_qS(O)_p(CH_2)_r$ or $S(O)_p(CH_2)_qO(CH_2)_r$, and more preferably a group represented by the formula: $S(CH_2)_n$, $S(CH_2)_qS(CH_2)_r$ or $S(CH_2)_qO(CH_2)_r$.

The compounds of Formula (I) can be prepared, for example, by the methods summarized by the following reaction scheme.

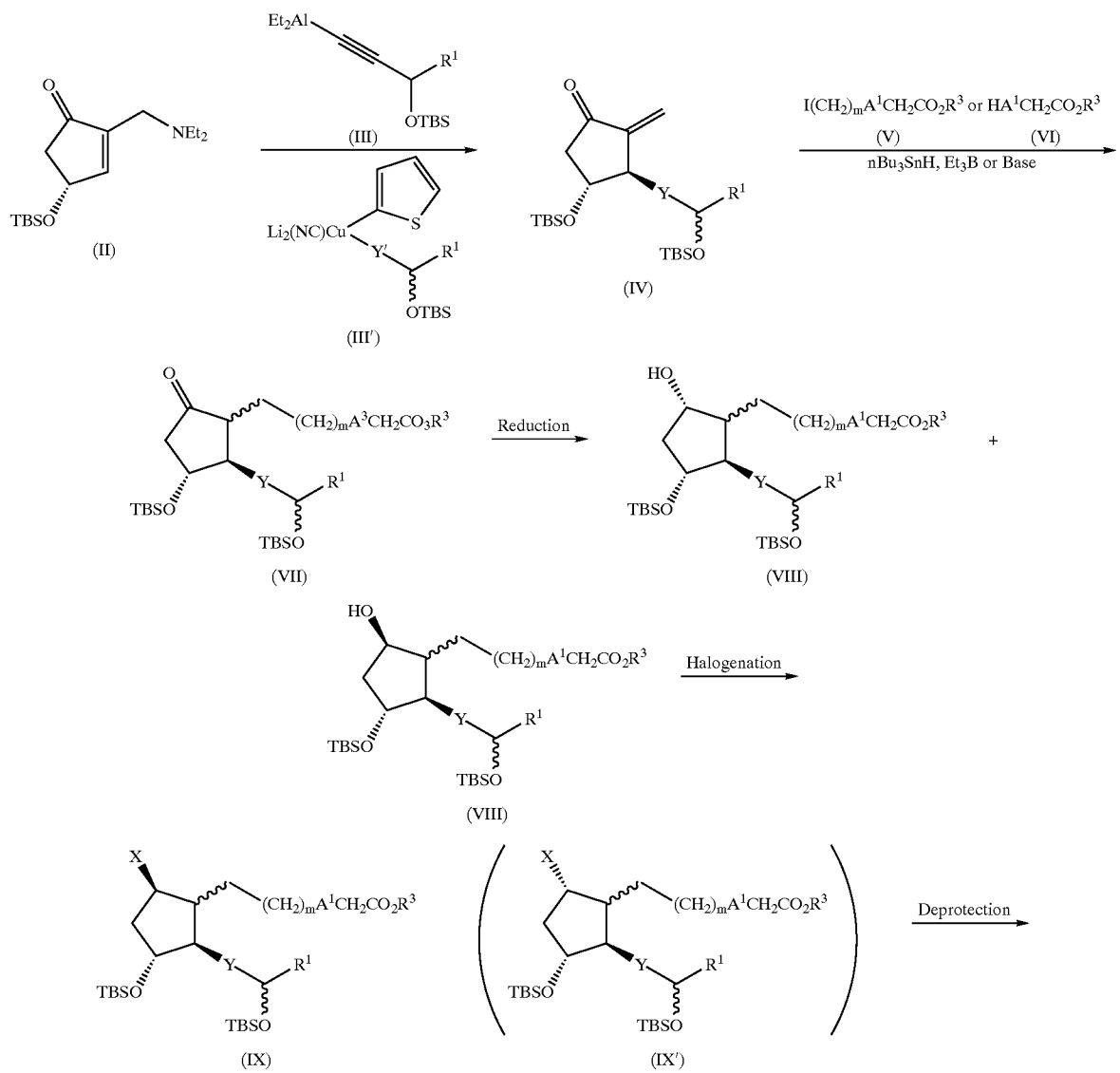

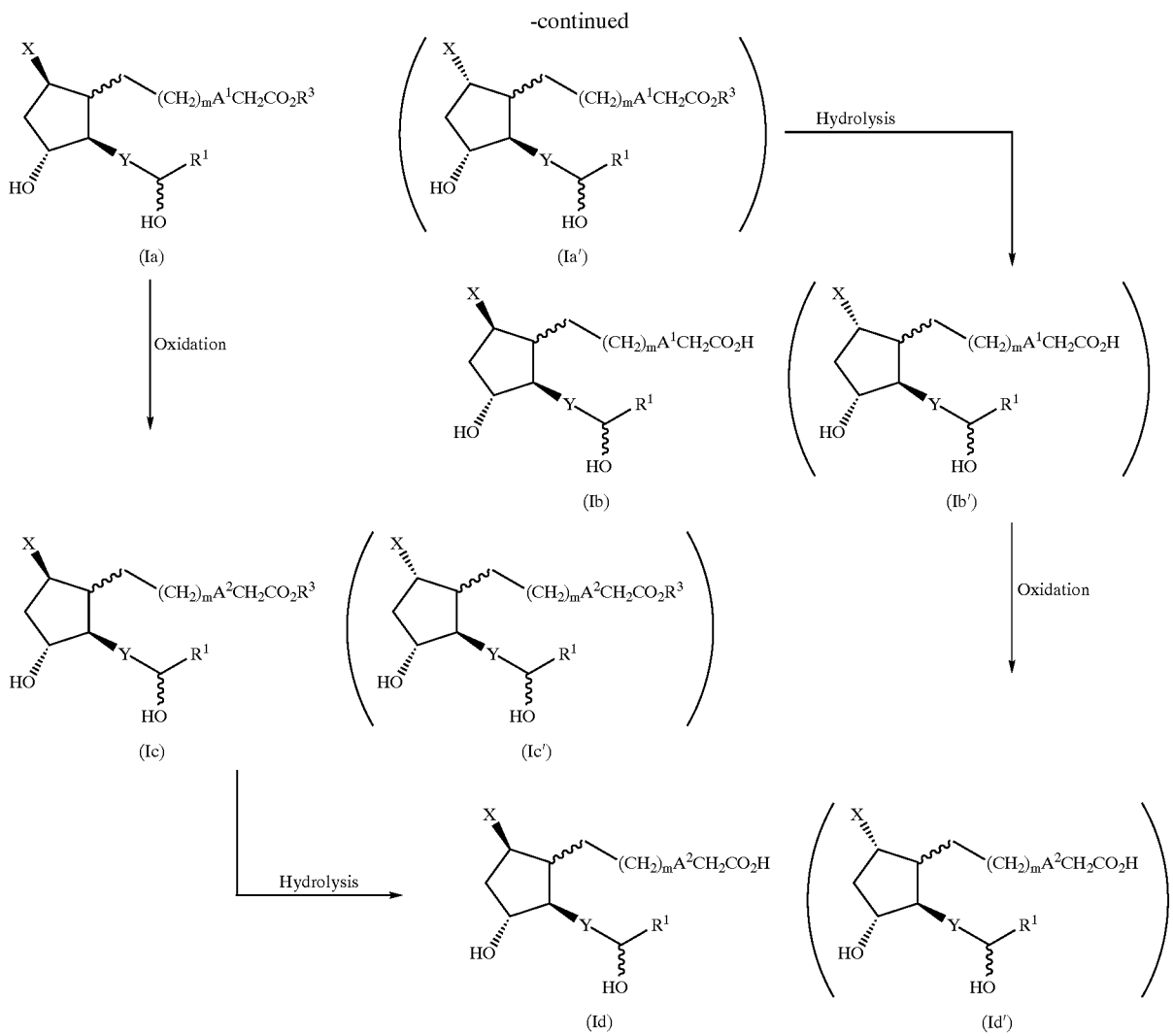

In the reaction scheme, $A^1$ is a group represented by the formula: $O(CH_2)_n$, $S(CH_2)_n$, $O(CH_2)_qO(CH_2)_r$, $O(CH_2)_qS(CH_2)_r$, $S(CH_2)_qS(CH_2)_r$ or $S(CH_2)_qO(CH_2)_r$ (wherein n, q and r are as defined above), $A^2$ is a group as defined for A except for p=O. Y' is an ethylene group or a vinylene group, $R^3$ is a $C_{1-10}$ alkyl group or a $C_{3-10}$ cycloalkyl group, TBS is a tert-butyldimethylsilyl group, and X, Y, $R^1$ and m are as defined above.

The above-mentioned reaction scheme is illustrated as follows:

(1) At first, a known compound of Formula (II) is reacted with 0.8 to 2.0 equivalents of a compound represented by Formula (III) or (III') in an inert solvent (e.g., benzene, toluene, tetrahydrofuran, diethyl ether, methylene chloride or n-hexane) at −78 to 30° C. according to the method of Sato et al. (*Journal of Organic Chemistry*, vol. 53, page 5590 (1988)) to stereospecifically give a compound of Formula (IV). Herein, the compound wherein Y is an ethylene group or a vinylene group (i.e., the compound wherein Y is Y') can be obtained by a reaction using a compound of Formula (III') at −78 to 0° C., and the compound wherein Y is an ethynylene group can be obtained by a reaction using a compound of Formula (III) at 0 to 30° C.

(2) The compound of Formula (IV) is reacted with 0.5 to 4 equivalents of a compound represented by Formula (V) or (VI) and 0.05 to 2 equivalents of a radical generating agent (e.g., azobisisobutyronitrile, azobiscyclohexanecarbonitrile, benzoyl peroxide or triethyl borane), if necessary, further using 1 to 5 equivalents of a radical reductant (e.g., tributyltin hydride, triphenyltin hydride, dibutyltin hydride or diphenyltin hydride) in an inert solvent (e.g., benzene, toluene, xylene, n-hexane, n-pentane or acetone) at −78 to 100° C. to give a compound of Formula (VII). Depending on the situation, the compound of Formula (VII) can be also obtained by a reaction using 0.05 to 2 equivalents of a base (e.g. an organic amine such as triethylamine, diisopropylamine, pyridine or dimethylaniline, or a base resin such as polyvinylpyrrolidone, diisopropylamlnomethyl—polystylene or (piperidinomethyl)polystylene) and, if necessary, using 0.01 to 0.5 equivalent of a bivalent palladium complex or complex salt (e.g. dichlorobis(acetonitrile)palladium(II), dichlorobis(benzonitrile)palladium(II) or palladium chloride) in an inert solvent (e.g., benzene, toluene, xylene, n-hexane, n-pentane or acetone) at −78 to 100° C.

(3) The compound of Formula (VII) is reacted with 0.5 to 5 equivalents of a reductant (e.g., potassium borohydride, sodium borohydride, lithium tricyanoborohydride, lithium tri-sec-butyl borohydride or diisobutylaluminum hydride—BHT (2,6-di-tert-butyl-p-cresol) in an organic solvent (e.g., tetrahydrofuran, diethyl ether, ethyl alcohol or methyl alcohol) at −78 to 40° C. to give compounds of Formulae (VIII) and (VIII'). These compounds of Formulae (VIII) and (VIII') can be purified by a conventional separation method such as column chromatography.

(4) The compound of Formula (VIII) or (VIII') is mesylated or tosylated, for example, with 1 to 6 equivalents of methanesulfonyl chloride or p-toluenesulfonyl chloride in a proper solvent such as pyridine or toluene (if necessary, in the presence of 0.8 to 6 equivalents of a base such as triethylamine or 4-dimethylaminopyridine) at −20 to 40° C., followed by chlorination with 1 to 16 equivalents of tetra-n-butylammonium chloride to give a compound of Formula (IX) or (IX') wherein X is a chlorine atom, respectively. Herein, bromination or fluorination can be also carried out in an ordinary manner. For example, bromination can be carried out by a reaction using 1 to 10 equivalents of carbon tetrabromide in the presence of 1 to 10 equivalents of triphenylphosphine and 1 to 10 equivalents of pyridine in acetonitrile. Fluorination can be carried out, for example, by a reaction with 5 to 20 equivalents of diethylaminosulfur trifluoride (DAST) in methylene chloride.

(5) The tert-butyldimethylsilyl group of the compound of Formula (IX) or (IX') is removed by using hydrofluoric acid, pyridinium poly(hydrogenfluoride) or hydrochloric acid in a solvent (e.g., methanol, ethanol, acetonitrile, a mixture thereof or a mixture of these solvent(s) and water) under conventional conditions to give a PG derivative of Formula (Ia) or (Ia') of the present invention.

(6) The compound of Formula (Ia) or (Ia') is hydrolyzed using 1 to 6 equivalents of a base in a conventional solvent for hydrolysis to give a PG derivative of Formula (Ib) or (Ib') of the present invention. Examples of the base to be used are lithium hydroxide and potassium carbonate, and examples of the solvent to be used are acetonitrile, acetone, methanol, ethanol, water and a mixture thereof.

Furthermore, the compound of Formula (Ia) is hydrolyzed by a reaction with an enzyme in a buffer solution such as phosphate buffer or tris-hydrochloride buffer, if necessary, by using an organic solvent (e.g. a water-miscible solvent such as acetone, methanol or ethanol) to give a PG derivative (Ib) of the present invention. Examples of the enzyme to be used are enzymes produced by microorganisms (e.g. enzymes produced by microorganisms belonging to Candida sp. or Pseudomonas sp.) and enzymes prepared from animal organs (e.g. enzymes prepared from pig liver or pig pancreas). Commercially available enzymes are, for example, lipase VII (derived from microorganism of Candida sp.; Sigma Co.;), lipase AY (derived from microorganism of Candida sp.; Amano Pharmaceutical. Co.), lipase PS (derived from microorganism of Pseudomonas sp.; Amano Pharmaceutical Co.), lipase MF (derived from microorganism of Pseudomonas sp.; Amano Pharmaceutical Co.), PLE (prepared from pig liver; Sigma Co.). lipase II (prepared from pig pancreas; Sigma Co.) or lipoprotein lipase (prepared from pig pancreas; Tokyo Kasei Kogyo Co.).

The amount of the enzyme to be used, while depending on the potency of the enzyme and the amount of the substrate (the compound of Formula (Ia)), is usually 0.1 to 20 parts by weight based on the substrate, and the reaction temperature is from 25 to 50° C., preferably 30 to 40° C.

(7) The compound of Formula (Ia) or (Ia') is oxidized using an oxidant such as sodium metaperiodate, hydrogen peroxide, peracetic acid, m-chloroperbenzoic acid or tert-butyl hydroxyperoxide in diethyl ether, methanol, ethanol, methylene chloride, water or a mixture thereof at −20 to 50° C. to give a PG derivative of Formula (Ic) or (Ic') of the present invention.

(8) The compound of Formula (Ic) or (Ic') is hydrolyzed in the similar manner as described in the above (6) to give a PG derivative of Formula (Id) or (Id') of the present invention. In addition, the PG derivative of Formula (Ib) or (Ib') is oxidized in the similar manner as described in the above (7) to give a PG derivative of Formula (Id) or (Id') of the present invention.

Representative compounds of the present invention are described bellow.

| Compound | X | Y | m | A | $R^1$ | $R^2$ | 8-position | 15-position |
|---|---|---|---|---|---|---|---|---|
| 1 | β-Cl | C≡C | 2 | $SCH_2$ | cyclohexyl | tert-butyl | α | α |
| 2 | β-Cl | C≡C | 0 | $S(CH_2)_3$ | cyclohexyl | tert-butyl | α | α |
| 3 | β-Cl | C≡C | 2 | $SCH_2$ | cyclohexyl | cyclohexyl | α | α |
| 4 | β-Cl | C≡C | 0 | $S(CH_2)_3$ | cyclohexyl | cyclohexyl | α | α |
| 5 | β-Cl | C≡C | 2 | $SCH_2$ | cyclohexyl | ethyl | α | α |
| 6 | β-Cl | C≡C | 2 | $S(O)CH_2$ | cyclohexyl | ethyl | α | α |
| 7 | β-Cl | C≡C | 2 | $S(O)CH_2$ | cyclohexyl | ethyl | α | β |
| 8 | β-Cl | C≡C | 2 | $S(O)_2CH_2$ | cyclohexyl | ethyl | α | α |
| 9 | β-Cl | C≡C | 1 | $SCH_2$ | cyclohexyl | methyl | α | α |
| 10 | β-Cl | C≡C | 1 | $S(CH_2)_2$ | cyclohexyl | methyl | α | α |
| 11 | β-Cl | C≡C | 1 | $S(O)(CH_2)_2$ | cyclohexyl | methyl | α | α |
| 12 | β-Cl | C≡C | 1 | $S(CH_2)_3$ | cyclohexyl | methyl | α | α |
| 13 | β-Cl | C≡C | 0 | $S(CH_2)_3$ | cyclohexyl | methyl | α | α |
| 14 | β-Cl | C≡C | 0 | $S(O)(CH_2)_3$ | cyclohexyl | methyl | α | α |
| 15 | β-Cl | C≡C | 0 | $S(O)_2(CH_2)_3$ | cyclohexyl | methyl | α | α |
| 16 | β-Cl | C≡C | 2 | $SCH_2$ | cyclohexyl | hydrogen | α | α |
| 17 | β-Cl | C≡C | 2 | $S(O)CH_2$ | cyclohexyl | hydrogen | α | α |
| 18 | β-Cl | C≡C | 2 | $S(O)_2CH_2$ | cyclohexyl | hydrogen | α | α |
| 19 | β-Cl | C≡C | 0 | $S(CH_2)_3$ | cyclohexyl | hydrogen | α | α |
| 20 | β-Cl | C≡C | 0 | $S(O)(CH_2)_3$ | cyclohexyl | hydrogen | α | α |
| 21 | β-Cl | C≡C | 0 | $S(O)_2(CH_2)_3$ | cyclohexyl | hydrogen | α | α |
| 22 | α-Cl | C≡C | 2 | $SCH_2$ | cyclohexyl | hydrogen | α | α |
| 23 | β-Br | C≡C | 2 | $SCH_2$ | cyclohexyl | hydrogen | α | α |
| 24 | α-Cl | C≡C | 0 | $S(CH_2)_3$ | cyclohexyl | hydrogen | α | α |
| 25 | α-Br | C≡C | 0 | $S(CH_2)_3$ | cyclohexyl | hydrogen | α | α |
| 26 | F | C≡C | 2 | $SCH_2$ | cyclohexyl | hydrogen | α | α |

-continued

| Compound | X | Y | m | A | R¹ | R² | 8-position | 15-position |
|---|---|---|---|---|---|---|---|---|
| 27 | β-Cl | C≡C | 2 | SCH₂ | cyclopentyl | methyl | β | α |
| 28 | β-Cl | C≡C | 0 | S(CH₂)₃ | cyclopentyl | methyl | α | α |
| 29 | β-Cl | C≡C | 2 | SCH₂ | cyclopentyl | hydrogen | β | α |
| 30 | β-Cl | C≡C | 2 | S(O)CH₂ | cyclopentyl | hydrogen | α | α |
| 31 | β-Cl | C≡C | 2 | S(O)₂CH₂ | cyclopentyl | hydrogen | α | α |
| 32 | β-Cl | C≡C | 2 | SCH₂ | cycloheptyl | hydrogen | α | α |
| 33 | β-Cl | C≡C | 0 | S(CH₂)₃ | cycloheptyl | hydrogen | α | α |
| 34 | β-Cl | C≡C | 2 | SCH₂ | cyclopentylmethyl | methyl | α | α |
| 35 | β-Cl | C≡C | 0 | S(CH₂)₃ | cyclopentylmethyl | methyl | α | α |
| 36 | β-Cl | C≡C | 2 | SCH₂ | cyclopentylmethyl | hydrogen | α | α |
| 37 | β-Cl | C≡C | 0 | S(CH₂)₄ | cyclopentylmethyl | hydrogen | α | α |
| 38 | α-Cl | C≡C | 2 | SCH₂ | cyclopentylmethyl | hydrogen | α | α |
| 39 | β-Cl | C≡C | 0 | S(CH₂)₃ | cyclohexylmethyl | hydrogen | α | α |
| 40 | β-Cl | C≡C | 0 | S(CH₂)₃ | (S)-2-methylhexyl | hydrogen | α | α |
| 41 | β-Cl | C≡C | 0 | S(CH₂)₃ | (R)-2-methylhexyl | hydrogen | α | α |
| 42 | β-Cl | C≡C | 0 | S(CH₂)₃ | (S)-2,6-dimethyl-5-heptenyl | hydrogen | α | α |
| 43 | β-Cl | C≡C | 0 | S(CH₂)₃ | (R)-2,6-dimethyl-5-heptenyl | hydrogen | α | α |
| 44 | β-Cl | C≡C | 0 | S(CH₂)₃ | (S)-1-methyl-3-hexynyl | hydrogen | α | α |
| 45 | β-Cl | C≡C | 0 | S(CH₂)₃ | (R)-1-methyl-3-hexynyl | hydrogen | α | α |
| 46 | β-Cl | C≡C | 2 | OCH₂ | cyclohexyl | methyl | α | α |
| 47 | β-Cl | C≡C | 2 | OCH₂ | cyclohexyl | methyl | α | β |
| 48 | β-Cl | C≡C | 1 | OCH₂ | cyclohexyl | methyl | α | α |
| 49 | β-Cl | C≡C | 1 | O(CH₂)₂ | cyclohexyl | methyl | α | α |
| 50 | β-Cl | C≡C | 1 | O(CH₂)₃ | cyclohexyl | methyl | α | α |
| 51 | β-Cl | C≡C | 0 | O(CH₂)₃ | cyclohexyl | methyl | α | α |
| 52 | β-Cl | C≡C | 2 | OCH₂ | cyclohexyl | hydrogen | α | α |
| 53 | β-Cl | C≡C | 0 | O(CH₂)₃ | cyclohexyl | hydrogen | α | α |
| 54 | α-Cl | C≡C | 2 | OCH₂ | cyclohexyl | hydrogen | α | α |
| 55 | β-Br | C≡C | 2 | OCH₂ | cyclohexyl | hydrogen | α | α |
| 56 | α-Br | C≡C | 0 | O(CH₂)₃ | cyclohexyl | hydrogen | α | α |
| 57 | F | C≡C | 2 | OCH₂ | cyclohexyl | hydrogen | α | α |
| 58 | β-Cl | C≡C | 2 | OCH₂ | cyclopentyl | methyl | α | α |
| 59 | β-Cl | C≡C | 0 | O(CH₂)₃ | cyclopentyl | methyl | α | α |
| 60 | β-Cl | C≡C | 2 | OCH₂ | cyclopentyl | hydrogen | α | α |
| 61 | β-Cl | C≡C | 2 | OCH₂ | cycloheptyl | hydrogen | α | α |
| 62 | β-Cl | C≡C | 0 | O(CH₂)₃ | cycloheptyl | hydrogen | α | α |
| 63 | β-Cl | C≡C | 2 | OCH₂ | cyclopentylmethyl | methyl | β | α |
| 64 | β-Cl | C≡C | 0 | O(CH₂)₃ | cyclopentylmethyl | methyl | α | α |
| 65 | β-Cl | C≡C | 2 | OCH₂ | cyclopentylmethyl | hydrogen | β | α |
| 66 | β-Cl | C≡C | 0 | O(CH₂)₃ | cyclopentylmethyl | hydrogen | α | α |
| 67 | β-Cl | C≡C | 2 | OCH₂ | cyclopentylmethyl | hydrogen | α | β |
| 68 | β-Cl | C≡C | 2 | OCH₂ | cyclohexylmethyl | hydrogen | α | α |
| 69 | β-Cl | C≡C | 0 | O(CH₂)₃ | cyclohexylmethyl | hydrogen | α | α |
| 70 | β-Cl | C≡C | 0 | O(CH₂)₃ | (S)-2-methylhexyl | hydrogen | α | α |
| 71 | β-Cl | C≡C | 0 | O(CH₂)₃ | (R)-2-methylhexyl | hydrogen | α | α |
| 72 | β-Cl | C≡C | 0 | O(CH₂)₃ | (S)-2,6-dimethyl-5-heptenyl | hydrogen | α | α |
| 73 | β-Cl | C≡C | 0 | O(CH₂)₃ | (R)-2,6-dimethyl-5-heptenyl | hydrogen | α | α |
| 74 | β-Cl | C≡C | 0 | O(CH₂)₃ | (S)-1-methyl-3-hexynyl | hydrogen | α | α |
| 75 | β-Cl | C≡C | 0 | O(CH₂)₃ | (R)-1-methyl-3-hexynyl | hydrogen | α | α |
| 76 | β-Cl | C≡C | 0 | S(CH₂)₃S | cyclohexyl | methyl | α | α |
| 77 | β-Cl | C≡C | 0 | S(CH₂)₂S | cyclohexyl | methyl | α | α |
| 78 | β-Cl | C≡C | 0 | S(O)(CH₂)₂S(O) | cyclohexyl | methyl | α | α |
| 79 | β-Cl | C≡C | 0 | SCH₂S | cyclohexyl | methyl | α | α |
| 80 | β-Cl | C≡C | 0 | SCH₂SCH₂ | cyclohexyl | methyl | α | α |
| 81 | β-Cl | C≡C | 0 | S(O)₂CH₂S(O)₂CH₂ | cyclohexyl | methyl | α | α |
| 82 | β-Cl | C≡C | 1 | SCH₂S | cyclohexyl | methyl | α | α |
| 83 | β-Cl | C≡C | 1 | S(CH₂)₂S | cyclohexyl | methyl | α | α |
| 84 | β-Cl | C≡C | 0 | S(CH₂)₂O | cyclohexyl | methyl | α | α |
| 85 | β-Cl | C≡C | 0 | S(CH₂)₃O | cyclohexyl | methyl | α | α |
| 86 | β-Cl | C≡C | 0 | S(O)(CH₂)₂O | cyclohexyl | methyl | α | α |
| 87 | β-Cl | C≡C | 0 | S(O)₂(CH₂)₂O | cyclohexyl | methyl | α | α |
| 88 | β-Cl | C≡C | 0 | S(CH₂)₃S | cyclohexyl | hydrogen | α | α |
| 89 | β-Cl | C≡C | 0 | S(CH₂)₂S | cyclohexyl | hydrogen | α | α |
| 90 | β-Cl | C≡C | 0 | SCH₂S | cyclohexyl | hydrogen | α | α |
| 91 | β-Cl | C≡C | 0 | SCH₂SCH₂ | cyclohexyl | hydrogen | α | α |
| 92 | β-Cl | C≡C | 0 | S(O)(CH₂)₂S(O) | cyclohexyl | hydrogen | α | α |
| 93 | β-Cl | C≡C | 0 | S(CH₂)₂SCH₂ | cyclohexyl | hydrogen | α | α |
| 94 | β-Cl | C≡C | 0 | S(O)₂CH₂S(O)₂CH₂ | cyclohexyl | hydrogen | α | α |
| 95 | β-Cl | C≡C | 1 | SCH₂S | cyclohexyl | hydrogen | α | α |
| 96 | β-Cl | C≡C | 1 | S(CH₂)₂S | cyclohexyl | hydrogen | α | α |
| 97 | β-Cl | C≡C | 0 | S(CH₂)₂O | cyclohexyl | hydrogen | α | α |
| 98 | β-Cl | C≡C | 0 | S(CH₂)₃O | cyclohexyl | hydrogen | α | α |
| 99 | β-Cl | C≡C | 0 | S(O)(CH₂)₂O | cyclohexyl | hydrogen | α | α |
| 100 | β-Cl | (E)CH=CH | 2 | SCH₂ | cyclohexyl | methyl | α | α |
| 101 | β-Cl | (E)CH=CH | 2 | SCH₂ | cyclohexyl | hydrogen | α | α |
| 102 | β-Cl | (E)CH=CH | 0 | S(CH₂)₃ | cyclohexyl | methyl | α | α |

-continued

| Compound | X | Y | m | A | R¹ | R² | 8-position | 15-position |
|---|---|---|---|---|---|---|---|---|
| 103 | β-Cl | (E)CH=CH | 0 | S(CH$_2$)$_3$ | cyclohexyl | hydrogen | α | α |
| 104 | β-Cl | (E)CH=CH | 0 | S(O)(CH$_2$)$_3$ | cyclohexyl | hydrogen | α | α |
| 105 | β-Cl | (E)CH=CH | 0 | S(O)$_2$(CH$_2$)$_3$ | cyclohexyl | hydrogen | α | α |
| 106 | β-Cl | (E)CH=CH | 0 | S(CH$_2$)$_2$S | cyclohexyl | methyl | α | α |
| 107 | β-Cl | (E)CH=CH | 0 | S(CH$_2$)$_2$S | cyclohexyl | hydrogen | α | α |
| 108 | β-Cl | (E)CH=CH | 0 | S(O)(CH$_2$)$_2$S(O) | cyclohexyl | hydrogen | α | α |
| 109 | β-Cl | (E)CH=CH | 0 | S(O)$_2$(CH$_2$)$_2$S(O)$_2$ | cyclohexyl | hydrogen | α | α |
| 110 | β-Cl | (E)CH=CH | 2 | OCH$_2$ | cyclohexyl | methyl | α | α |
| 111 | β-Cl | (E)CH=CH | 2 | OCH$_2$ | cyclohexyl | hydrogen | α | α |
| 112 | β-Cl | (E)CH=CH | 0 | S(CH$_2$)$_2$O | cyclohexyl | methyl | α | α |
| 113 | β-Cl | (E)CH=CH | 0 | S(CH$_2$)$_2$O | cyclohexyl | hydrogen | α | α |
| 114 | β-Cl | (E)CH=CH | 0 | S(O)(CH$_2$)$_2$O | cyclohexyl | hydrogen | α | α |
| 115 | β-Cl | (E)CH=CH | 0 | S(O)$_2$(CH$_2$)$_2$O | cyclohexyl | hydrogen | α | α |
| 116 | β-Cl | (E)CH=CH | 0 | S(CH$_2$)$_3$ | cyclopentylmethyl | hydrogen | α | α |
| 117 | β-Cl | (E)CH=CH | 0 | S(CH$_2$)$_2$S | cyclopentylmethyl | hydrogen | α | α |
| 118 | β-Cl | (E)CH=CH | 0 | S(CH$_2$)$_2$O | cyclopentylmethyl | hydrogen | α | α |
| 119 | β-Cl | (Z)CH=CH | 0 | S(CH$_2$)$_3$ | cyclohexyl | hydrogen | α | α |
| 120 | β-Cl | (Z)CH=CH | 0 | S(CH$_2$)$_2$S | cyclohexyl | hydrogen | α | α |
| 121 | β-Cl | (Z)CH=CH | 0 | S(CH$_2$)$_2$O | cyclohexyl | hydrogen | α | α |
| 122 | β-Cl | CH$_2$CH$_2$ | 2 | SCH$_2$ | cyclohexyl | methyl | α | α |
| 123 | β-Cl | CH$_2$CH$_2$ | 2 | SCH$_2$ | cyclohexyl | hydrogen | α | α |
| 124 | β-Cl | CH$_2$CH$_2$ | 0 | S(CH$_2$)$_3$ | cyclohexyl | methyl | α | α |
| 125 | β-Cl | CH$_2$CH$_2$ | 0 | S(O)(CH$_2$)$_3$ | cyclohexyl | methyl | α | α |
| 126 | β-Cl | CH$_2$CH$_2$ | 0 | S(O)$_2$(CH$_2$)$_3$ | cyclohexyl | methyl | α | α |
| 127 | β-Cl | CH$_2$CH$_2$ | 0 | S(CH$_2$)$_3$ | cyclohexyl | hydrogen | α | α |
| 128 | β-Cl | CH$_2$CH$_2$ | 0 | S(O)(CH$_2$)$_3$ | cyclohexyl | hydrogen | α | α |
| 129 | β-Cl | CH$_2$CH$_2$ | 0 | S(O)$_2$(CH$_2$)$_3$ | cyclohexyl | hydrogen | α | α |
| 130 | β-Cl | CH$_2$CH$_2$ | 0 | S(CH$_2$)$_2$S | cyclohexyl | methyl | α | α |
| 131 | β-Cl | CH$_2$CH$_2$ | 0 | S(CH$_2$)$_2$S | cyclohexyl | hydrogen | α | α |
| 132 | β-Cl | CH$_2$CH$_2$ | 0 | S(O)(CH$_2$)$_2$S(O) | cyclohexyl | hydrogen | α | α |
| 133 | β-Cl | CH$_2$CH$_2$ | 0 | S(O)$_2$(CH$_2$)$_2$S(O)$_2$ | cyclohexyl | hydrogen | α | α |
| 134 | β-Cl | CH$_2$CH$_2$ | 2 | OCH$_2$ | cyclohexyl | methyl | α | α |
| 135 | β-Cl | CH$_2$CH$_2$ | 2 | OCH$_2$ | cyclohexyl | hydrogen | α | α |
| 136 | β-Cl | CH$_2$CH$_2$ | 0 | S(CH$_2$)$_2$O | cyclohexyl | methyl | α | α |
| 137 | β-Cl | CH$_2$CH$_2$ | 0 | S(CH$_2$)$_2$O | cyclohexyl | hydrogen | α | α |
| 138 | β-Cl | CH$_2$CH$_2$ | 0 | S(O)(CH$_2$)$_2$O | cyclohexyl | hydrogen | α | α |
| 139 | β-Cl | CH$_2$CH$_2$ | 0 | S(O)$_2$(CH$_2$)$_2$O | cyclohexyl | hydrogen | α | α |
| 140 | β-Cl | CH$_2$CH$_2$ | 0 | S(CH$_2$)$_3$O | cyclohexyl | methyl | α | α |
| 141 | β-Cl | CH$_2$CH$_2$ | 0 | S(CH$_2$)$_3$O | cyclohexyl | hydrogen | α | α |
| 142 | β-Cl | CH$_2$CH$_2$ | 0 | S(CH$_2$)$_2$O | cyclohexyl | tert-butyl | α | α |
| 143 | β-Cl | CH$_2$CH$_2$ | 0 | SCH$_2$OCH$_2$ | cyclohexyl | methyl | α | α |
| 144 | β-Cl | CH$_2$CH$_2$ | 0 | SCH$_2$OCH$_2$ | cyclohexyl | hydrogen | α | α |
| 145 | β-Cl | CH$_2$CH$_2$ | 0 | S(CH$_2$)$_2$O | cyclopentyl | methyl | α | α |
| 146 | β-Cl | CH$_2$CH$_2$ | 0 | S(CH$_2$)$_2$O | cyclopentyl | hydrogen | α | α |
| 147 | β-Cl | CH$_2$CH$_2$ | 0 | S(CH$_2$)$_2$O | cycloheptyl | methyl | α | α |
| 148 | β-Cl | CH$_2$CH$_2$ | 0 | S(CH$_2$)$_2$O | cycloheptyl | hydrogen | α | α |
| 149 | β-Cl | CH$_2$CH$_2$ | 0 | S(CH$_2$)$_2$O | cyclohexylmethyl | hydrogen | α | α |
| 150 | β-Br | CH$_2$CH$_2$ | 0 | S(CH$_2$)$_2$O | n-pentyl | hydrogen | β | α |
| 151 | β-Cl | CH$_2$CH$_2$ | 0 | S(CH$_2$)$_2$O | n-pentyl | hydrogen | α | α |
| 152 | α-Cl | CH$_2$CH$_2$ | 0 | S(CH$_2$)$_2$O | n-pentyl | hydrogen | α | α |
| 153 | β-Cl | CH$_2$CH$_2$ | 0 | SCH$_2$SCH$_2$ | cyclohexyl | methyl | α | α |
| 154 | β-Cl | CH$_2$CH$_2$ | 0 | SCH$_2$SCH$_2$ | cyclohexyl | hydrogen | α | α |
| 155 | β-Cl | CH$_2$CH$_2$ | 0 | S(CH$_2$)$_2$S | cyclopentyl | methyl | α | α |
| 156 | β-Cl | CH$_2$CH$_2$ | 0 | S(CH$_2$)$_2$S | cyclopentyl | hydrogen | α | α |
| 157 | β-Cl | CH$_2$CH$_2$ | 0 | S(CH$_2$)$_2$S | cycloheptyl | methyl | α | α |
| 158 | β-Cl | CH$_2$CH$_2$ | 0 | S(CH$_2$)$_2$S | cycloheptyl | hydrogen | α | α |
| 159 | β-Cl | CH$_2$CH$_2$ | 0 | S(CH$_2$)$_2$S | cyclohexylmethyl | methyl | α | α |
| 160 | β-Cl | CH$_2$CH$_2$ | 0 | S(CH$_2$)$_2$S | cyclohexylmethyl | hydrogen | α | α |
| 161 | β-Cl | CH$_2$CH$_2$ | 0 | S(CH$_2$)$_2$S | n-pentyl | hydrogen | β | β |
| 162 | α-Cl | CH$_2$CH$_2$ | 0 | S(CH$_2$)$_2$S | n-pentyl | hydrogen | α | α |
| 163 | β-Cl | (Z)CH=CH | 0 | S(CH$_2$)$_2$O | cyclohexyl | methyl | α | α |
| 164 | F | (E)CH=CH | 0 | S(CH$_2$)$_2$O | cyclohexyl | methyl | α | α |
| 165 | F | (E)CH=CH | 0 | S(CH$_2$)$_2$O | cyclohexyl | hydrogen | α | α |
| 166 | β-Cl | (E)CH=CH | 0 | S(CH$_2$)$_2$O | cyclopentyl | hydrogen | α | β |
| 167 | β-Cl | (E)CH=CH | 0 | S(CH$_2$)$_2$O | (R)-2-methylhexyl | hydrogen | α | α |
| 168 | β-Cl | (E)CH=CH | 0 | S(CH$_2$)$_2$O | (S)-2-methylhexyl | hydrogen | α | α |
| 169 | β-Cl | (E)CH=CH | 0 | S(CH$_2$)$_2$O | (R)-1-methyl-3-hexynyl | hydrogen | α | α |
| 170 | β-Cl | (E)CH=CH | 0 | S(CH$_2$)$_2$O | (S)-1-methyl-3-hexynyl | hydrogen | α | α |
| 171 | β-Cl | (Z)CH=CH | 0 | S(CH$_2$)$_2$S | cyclohexyl | methyl | α | α |
| 172 | β-Cl | (E)CH=CH | 0 | S(CH$_2$)$_2$S | cyclopentyl | hydrogen | α | β |
| 173 | β-Cl | (E)CH=CH | 0 | S(CH$_2$)$_2$S | (R)-2-methylhexyl | hydrogen | α | α |
| 174 | β-Cl | (E)CH=CH | 0 | S(CH$_2$)$_2$S | (S)-2-methylhexyl | hydrogen | α | α |
| 175 | β-Cl | (E)CH=CH | 0 | S(O)(CH$_2$)$_2$S(O) | (R)-2-methylhexyl | hydrogen | α | α |
| 176 | β-Cl | (E)CH=CH | 0 | S(O)(CH$_2$)$_2$S(O) | (S)-2-methylhexyl | hydrogen | α | α |
| 177 | β-Cl | (E)CH=CH | 0 | S(CH$_2$)$_2$S | (R)-1-methyl-3-hexynyl | hydrogen | α | α |
| 178 | β-Cl | (E)CH=CH | 0 | S(CH$_2$)$_2$S | (S)-1-methyl-3-hexynyl | hydrogen | α | α |

-continued

| Compound | X | Y | m | A | R¹ | R² | 8-position | 15-position |
|---|---|---|---|---|---|---|---|---|
| 179 | α-Cl | C≡C | 0 | S(CH$_2$)$_2$O | cyclohexyl | methyl | α | α |
| 180 | α-Cl | C≡C | 0 | S(CH$_2$)$_2$O | cyclohexyl | hydrogen | α | α |
| 181 | β-Cl | C≡C | 0 | S(CH$_2$)$_2$O | cyclopentyl | hydrogen | α | α |
| 182 | β-Cl | C≡C | 0 | S(CH$_2$)$_2$O | cycloheptyl | hydrogen | α | α |
| 183 | β-Cl | C≡C | 0 | S(CH$_2$)$_2$O | cyclopentylmethyl | hydrogen | α | α |
| 184 | β-Cl | C≡C | 0 | S(CH$_2$)$_2$O | cyclohexylmethyl | hydrogen | α | α |
| 185 | β-Cl | C≡C | 0 | S(CH$_2$)$_2$O | (R)-2-methylhexyl | hydrogen | α | α |
| 186 | β-Cl | C≡C | 0 | S(CH$_2$)$_2$O | (S)-2-methylhexyl | hydrogen | α | α |
| 187 | β-Cl | C≡C | 0 | S(CH$_2$)$_2$O | (R)-2,6-dimethyl-5-heptenyl | hydrogen | α | α |
| 188 | β-Cl | C≡C | 0 | S(CH$_2$)$_2$O | (S)-2,6-dimethyl-5-heptenyl | hydrogen | α | α |
| 189 | β-Cl | C≡C | 0 | S(CH$_2$)$_2$S(O) | cyclohexyl | methyl | α | α |
| 190 | β-Cl | C≡C | 0 | S(CH$_2$)$_2$S(O) | cyclohexyl | hydrogen | α | α |
| 191 | β-Cl | C≡C | 0 | S(O)$_2$(CH$_2$)$_2$S(O)$_2$ | cyclohexyl | methyl | α | α |
| 192 | β-Cl | C≡C | 0 | S(O)$_2$(CH$_2$)$_2$S(O)$_2$ | cyclohexyl | hydrogen | α | α |
| 193 | α-Cl | C≡C | 0 | S(CH$_2$)$_2$S | cyclohexyl | methyl | α | α |
| 194 | α-Cl | C≡C | 0 | S(CH$_2$)$_2$S | cyclohexyl | hydrogen | α | α |
| 195 | β-Cl | C≡C | 0 | S(CH$_2$)$_2$S | cyclopentyl | hydrogen | α | α |
| 196 | β-Cl | C≡C | 0 | S(CH$_2$)$_2$S | cycloheptyl | hydrogen | α | α |
| 197 | β-Cl | C≡C | 0 | S(CH$_2$)$_2$S | cyclopentylmethyl | hydrogen | α | α |
| 198 | β-Cl | C≡C | 0 | S(CH$_2$)$_2$S | cyclohexylmethyl | hydrogen | α | α |
| 199 | β-Cl | C≡C | 0 | S(CH$_2$)$_2$S | (R)-2-methylhexyl | hydrogen | α | α |
| 200 | β-Cl | C≡C | 0 | S(CH$_2$)$_2$S | (S)-2-methylhexyl | hydrogen | α | α |
| 201 | β-Cl | C≡C | 0 | S(CH$_2$)$_2$S | (R)-2,6-dimethyl-5-heptenyl | hydrogen | α | α |
| 202 | β-Cl | C≡C | 0 | S(CH$_2$)$_2$S | (S)-2,6-dimethyl-5-heptenyl | hydrogen | α | α |
| 203 | α-Cl | C≡C | 0 | S(CH$_2$)$_2$S | (R)-2-methylhexyl | hydrogen | α | α |
| 204 | α-Cl | C≡C | 0 | S(CH$_2$)$_2$S | (S)-2-methylhexyl | hydrogen | β | β |
| 205 | F | C≡C | 0 | S(CH$_2$)$_2$S | (R)-2,6-dimethyl-5-heptenyl | hydrogen | α | α |
| 206 | F | C≡C | 0 | S(CH$_2$)$_2$S | (S)-2,6-dimethyl-5-heptenyl | hydrogen | α | α |

The compounds of the present invention can be administered systemically or topically, or orally or parenterally (intravenously) in conventional dosage forms. For example, the dosage form for oral administration includes tablets, powders, granules, dusting powders, capsules, solutions, emulsions or suspensions, each of which can be prepared according to conventional methods. The dosage form for intravenous administration includes aqueous or non-aqueous solutions, emulsions, suspensions or solid preparations to be dissolved in a solvent for injection immediately before use. Furthermore, the compounds of the present invention can be formulated into the form of inclusion compounds with α-, β- or γ-cyclodextrin, or methylated cyclodextrin. In addition, the compounds of the present invention can be administered by injection in the form of aqueous or non-aqueous solutions, emulsions, suspensions, etc. The dose is varied by the age, body weight, etc., but it is from 1 ng to 1 mg/day per adult, which can be administered in a single dose or divided doses.

BEST MODE FOR CARRYING OUT THE INVENTION

The present invention is illustrated in more details by the following examples and experiment, but it is not limited by these descriptions.

EXAMPLE 1

6-Thia-9-deoxy-9β-chloro-16,17,18,19,20-pentanor-15-cyclohexyl-13,14-didehydro-PGF$_1$α methyl ester (Compound 13)

(1) In toluene (80 ml) was dissolved (3S)-3-(tert-butyldimethylsiloxy)-3-cyclohexylprop-1-yne (6.58 g), and n-butyl lithium (3.0 M, hexane solution, 8.0 ml) was added at 0° C., followed by stirring at the same temperature for 30 minutes. To the solution was added diethylaluminum chloride (0.95 M, hexane solution, 29.0 ml) at 0° C., followed by stirring at room temperature for 30 minutes. To the solution was added (4R)-2-(N,N-diethylamino)methyl-4-(tert-butyldimethylsiloxy)cyclopent-2-en-1-one (0.25 M, toluene solution, 80.0 ml) at room temperature, followed by stirring for 15 minutes. The reaction solution, while stirring, was added to a mixture of hexane (190 ml), a saturated aqueous ammonium chloride solution (190 ml) and an aqueous hydrochloric acid solution (3 M, 56 ml), and the organic layer was separated and washed with a saturated aqueous sodium bicarbonate solution (50 ml). The resulting organic layer was dried over anhydrous magnesium sulfate, filtered and concentrated, and the resulting residue was purified by a silica gel column chromatography (developing solvent; hexane:ether=10:1) to give (3R,4R)-2-methylene-3-[(3S)-3-(tert-butyldimethylsiloxy)-3-cyclohexylprop-1-ynyl]-4-(tert-butyldimethylsiloxy)cyclopentan-1-one (7.92 g).

$^1$H-NMR(CDCl$_3$, 200 MHz) δ ppm; 0.07, 0.08 and 0.12 (3s, 12H), 0.88 (s, 18H), 0.92–1.92 (m, 11H), 2.32 (dd, J=17.8, 7.4 Hz, 1H), 2.71 (dd, J=17.8, 6.5 Hz, 1H), 3.48–3.58 (m, 1H), 4.11 (dd, J=6.2, 1.4 Hz, 1H), 4.20–4.32 (m, 1H), 5.55 (d, J=2.6 Hz, 1H), 6.13 (d, J=3.0 Hz, 1H);

IR(neat) cm$^{-1}$; 2930, 2850, 1735, 1640, 1470, 1380, 1255, 830, 770.

(21 To a toluene solution (32 ml) of the compound obtained in the above (1) (3.86 g) and methyl 5-mercaptopentanoate (1.64 g) was added triethyl borane (1.0 M, hexane solution, 0.81 ml) under an argon atmosphere at 0° C., followed by allowing to stand at the same temperature overnight. The reaction solution was purified by a silica gel column chromatography to give 6-thia-16,17,18,19,20-pentanor-15-cyclohexyl-13,14-didehydro-PGE$_1$ methyl ester 11,15-bis(tert-butyldimethylsilyl ether) (1.02 g).

$^1$H-NMR(CDCl$_3$, 200 MHz) δ ppm; 0.08 (s, 3H), 0.09 (s, 3H), 0.10 (s, 3H), 0.13 (s, 3H), 0.71–1.93 (m, 15H), 0.89 (s, 9H), 0.90 (s, 9H), 2.22 (dd, J=18.2, 5.9 Hz, 1 H), 2.33 (t, J=7.3 Hz, 2H), 2.40–2.59 (m, 1H), 2.53 (t, J=7.0 Hz, 2H), 2.71 (dd, J=18.2, 6.0 Hz, 1H), 2.73–2.96 (m, 2H), 3.09–3.22 (m, 1H), 3.67 (s, 3H), 4.08 (dd, J=6.3, 1.6 Hz, 1H), 4.29–4.41 (m, 1H);

IR(neat) cm$^{-1}$; 2951, 2929, 2855, 2236, 1746, 1472, 1463, 1451, 1406, 1361, 1252, 1202, 1109, 1065, 1006, 939, 898, 837, 778, 669, 587.

(3) A methyl alcohol solution (12.8 ml) of the compound obtained in the above (2) (800 mg) was cooled to 0° C., and potassium borohydride (138 mg) was added, followed by stirring for 40 minutes. A saturated aqueous ammonium chloride solution was added, followed by extraction with ethyl acetate. The organic layer was washed with a saturated aqueous ammonium chloride solution and a saturated aqueous sodium chloride solution, dried over anhydrous magnesium sulfate and filtered. The filtrate was concentrated under reduced pressure, and the resulting residue was purified by a silica gel column chromatography (developing solvent; n-hexane:ethyl acetate=7:1 to 4:1) to give 6-thia-16,17,18, 19,20-pentanor-15-cyclohexyl-13,14-didehydro-PGF$_1\alpha$ methyl ester 11,15-bis(tert-butyldimethylsilyl ether) (500 mg) and 6-thia-16,17,18,19,20-pentanor-15-cyclohexyl-13, 14-didehydro-PGF$_1\beta$ methyl ester 11,15-bis(tert-butyldimethylsilyl ether) (248 mg).

6-Thia-16,17,18,19,20-pentanor-15-cyclohexyl-13, 14-didehydro-PGF$_1\alpha$ methyl ester 11,15-bis(tert-butyldimethylsilyl ether)

$^1$H-NMR(CDCl$_3$, 200 MHz) δ ppm; 0.08 (s, 3H), 0.09 (s, 3H), 0.10 (s, 6H), 0.84–2.24 (m, 18H), 0.89 (s, 9H), 0.90 (s, 9H), 2.34 (t, J=7.4 Hz, 2H), 2.50–2.64 (m, 4H), 2.74–2.88 (m, 2H), 3.67 (s, 3H), 4.08 (dd, J=5.9, 1.8 Hz, 1H), 4.18–4.33 (m, 1H);

IR(neat) cm$^{-1}$; 3435, 2928, 2854, 2232, 1741, 1471, 1462, 1450, 1385, 1361, 1251, 1205, 1110, 1062, 1005, 925, 898, 836, 776, 669.

6-Thia-16,17,18,19,20-pentanor-15-cyclohexyl-13, 14-didehydro-PGF$_1\beta$ methyl ester 11,15-bis(tert-butyldimethylsilyl ether)

$^1$H-NMR(CDCl$_3$, 200 MHz) δ ppm; 0.07 (s, 3H), 0.08 (s, 6H), 0.11 (s, 3H), 0.82–2.08 (m, 18H), 0.88 (s, 9H), 0.90 (s, 9H), 2.27–2.40 (m, 3H), 2.47 (dd, J=13.2, 10.3 Hz, 1H), 2.58 (t, J=6.9 Hz, 2H), 2.65 (d, J=2.9 Hz, 1H), 2.99 (dd, J=13.2, 4.2 Hz, 1H), 3.68 (s, 3H), 4.04–4.30 (m, 3H);

IR(neat) cm$^{-1}$; 3435, 2928, 2855, 2233, 1742, 1472, 1462, 1450, 1361, 1252, 1215, 1175, 1100, 1065, 1005, 897, 836, 777, 669.

(4) To a pyridine solution (3.9 ml) of 6-thia-16,17,18,19, 20-pentanor-15-cyclohexyl-13,14-didehydro-PGF$_1\alpha$ methyl ester 11,15-bis(tert-butyldimethylsilyl ether) obtained in the above (3) (490 mg) was added methanesulfonyl chloride (0.12 ml) under an argon stream at 0° C., followed by stirring at room temperature for 2 hours. To the solution was added a toluene solution (3.9 ml) of tetra-n-butylammonium chloride (1.74 g), followed by stirring at 45° C. overnight. To this was added water and, after extraction with n-hexane, the extract was washed with a saturated aqueous sodium chloride solution, dried over anhydrous magnesium sulfate and filtered. The filtrate was concentrated under reduced pressure, and the resulting crude product was purified by a silica gelcolumn chromatography (developing solvent; n-hexane:ethyl acetate=49:1) to give 6-thia-9-deoxy-9β-chloro-16,17,18,19,20-pentanor-15-cyclohexyl-13,14-didehydro-PGF$_1\alpha$ methyl ester 11,15-bis(tert-butyldimethylsilyl ether) (410 mg).

$^1$H-NMR(CDCl$_3$, 200 MHz) δ ppm; 0.08 (s, 6H), 0.09 (s, 3H), 0.11 (s, 3H), 0.78–0.92 (m, 15H), 0.88 (s, 9H), 0.90 (s, 9H), 2.14–2.40 (m, 3H), 2.34 (t, J=7.0 Hz, 2H), 2.51–2.64 (m, 1H), 2.58 (t, J=7.0 Hz, 2H), 2.81 (d, J=5.3 Hz, 2H), 3.68 (s, 3H), 4.03–4.34 (m, 2H), 4.09 (dd, J=6.2, 1.8 Hz, 1H);

IR(neat) cm$^{-1}$; 3400, 2929, 2855, 2232, 1742, 1471, 1462, 1451, 1384, 1361, 1252, 1157, 1100, 927, 898, 836, 777, 668.

(5) To a methyl alcohol solution (12.4 ml) of the compound obtained in the above (4) (400 mg) was added conc. hydrochloric acid (0.062 ml) at room temperature, followed by stirring for 2 hours. The reaction solution was added to a mixture of ethyl acetate and a saturated aqueous sodium bicarbonate solution, and the organic layer was separated. The aqueous layer was extracted with ethyl acetate, and the organic layers were combined, washed with a saturated aqueous sodium bicarbonate solution, dried over anhydrous magnesium sulfate and filtered. The filtrate was concentrated under reduced pressure, and the resulting crude product was purified by a silica gel column chromatography (developing solvent; n-hexane:ethyl acetate=3:1 to 1:1) to give the title compound (238 mg).

$^1$H-NMR(CDCl$_3$, 200 MHz) δ ppm; 0.95–1.92 (m, 15H), 2.00 (d, J=5.9 Hz, 1H), 2.12 (d, J=4.0 Hz, 1H), 2.22–2.46 (m, 3H), 2.36 (t, J=7.0 Hz, 2H), 2.53–21.68 (m, 1H), 2.59 (t, J=6.9 Hz, 2H), 2.79 (dd, J=13.6, 4.8 Hz, 1H), 2.88 (dd, J=13.6, 5.3 Hz, 1H), 3.68 (s, 3H), 4.09–4.28 (m, 2H), 4.32–4.47 (m, 1H);

IR(neat) cm$^{-1}$; 3400, 2926, 2852, 2235, 1739, 1723, 1449, 1275, 1210, 1174, 1011, 893, 832, 503.

EXAMPLE 2

6-Thia-9-deoxy-9β-chloro-16,17,18,19,20-pentanor-15-cyclohexyl-13,14-didehydro-PGF$_1\alpha$ (Compound 19)

To a methyl alcohol (10.6 ml)—water (1.06 ml) solution of the compound obtained in Example 1(133 mg) was added lithium hydroxide monohydrate (67 mg), followed by stirring at room temperature overnight. The mixture was made weakly acidic with 1 M hydrochloric acid and extracted with ethyl acetate, and the extract was washed with a saturated aqueous sodium chloride solution, dried over anhydrous magnesium sulfate and filtered. The filtrate was concentrated under reduced pressure, and the resulting crude product was purified by a silica gel column chromatography (developing solvent; ethyl acetate) to give the title compound (120 mg).

$^1$H-NMR(CDCl$_3$, 200 MHz) δ ppm; 0.92–2.01 (m, 21H), 2.14–3.06 (m, 9H), 2.72 (dd, J=13.7, 5.3 Hz, 1H), 2.94 (dd, J=13.7, 4.9 Hz, 1H), 4.09–4.27 (m, 2H), 4.34–4.47 (m, 1H);

IR(neat) cm$^{-1}$; 3368, 2927, 2852, 2236, 1708, 1450, 1412, 1278, 1682, 1007, 893, 847, 758.

EXAMPLE 3

4-Oxa-9-deoxy-9β-chloro-16,17,18,19,20-pentanor-15-cyclohexyl-13,14-didehydro-PGF$_1\alpha$ methyl ester (Compound 46)

(1) To a toluene solution (13.5 ml) of the compound obtained in Example 1(1) (1.60 g) and methyl 4-oxa-6-iodohexanoate (2.16 g) were added tributyltin hydride (2.25 ml) and triethyl borane (1.0 M, hexane solution, 0.34 ml) under argon atmosphere at 0° C., followed by allowing to stand at the same temperature overnight. The reaction solution was purified by a silica gel column chromatography to give 4-oxa-16,17,18,19,20-pentanor-15-cyclohexyl-13,14-didehydro-PGE$_1$ methyl ester 11,15-bis(tert-butyldimethylsilyl ether) (1.22 g).

$^1$H-NMR(CDCl$_3$, 200 MHz) δ ppm; 0.08 (s, 3H), 0.09 (s, 3H), 0.10 (s, 3H), 0.12 (s, 3H), 0.78–1.94 (m, 15H), 0.89 (s, 9H), 0.90 (s, 9H), 2.07–2.30 (m, 1H), 2.17 (dd, J=18.2, 7.0 Hz, 1H), 2.52–2.77 (m, 2H), 2.61 (t, J=6.6 Hz, 2H), 3.44 (t, J=6.2 Hz, 2H), 3.60–3.84 (m, 2H), 3.70 (s, 3H), 4.08 (dd, J=6.3, 1.4 Hz, 1H), 4.22–4.36 (m, 11H);

IR(neat) cm$^{-1}$; 2952, 2929, 2856, 2235, 1746, 1472, 1463, 1437, 1406, 1361, 1252, 1196, 1176, 1104, 1006, 939, 898, 837, 778, 669.

(2) Following the substantially same manner as in Example 1(3) using the compound obtained in the above (1), thereby the compounds described below were obtained.

4-Oxa-16,17,18,19,20-pentanor-15-cyclohexyl-13,14-didehydro-PGF$_1$α methyl ester 11,15-bis(tert-butyldimethylsilyl ether)

$^1$H-NMR(CDCl$_3$, 200 MHz) δ ppm; 0.08 (s, 3H), 0.09 (2s, 6H), 0.10 (s, 3H), 0.78–21 (m, 18H), 0.88 (s, 9H), 0.90 (s, 9H), 2.41–2.52 (m, 1H), 2.58 (t, J=6.6 Hz, 2H), 2.63 (d, J=8.8 Hz, 1H), 3.41–3.54 (m, 2H), 3.69 (s, 3H), 3.70 (t, J=6.5 Hz, 2H), 4.02–4.31 (m, 2H), 4.07 (dd, J=6.2, 2.0 Hz, 1H);

IR(neat) cm$^{-1}$; 3468, 2929, 2855, 2229, 1745, 1472, 1463, 1451, 1361, 1337, 1252, 1196, 1106, 1072, 1005, 963, 939, 898, 836, 776, 668.

4-Oxa-16,17,18,19,20-pentanor-15-cyclohexyl-13,14-didehydro-PGF$_1$β methyl ester 11,15-bis(tert-butyldimethylsilyl ether)

$^1$H-NMR(CDCl$_3$, 200 MHz) δ ppm; 0.07 (s, 3H), 0.08 (s, 6H), 0.11 (s, 3H), 0.78–1.95 (m, 18H), 0.88 (s, 9H), 0.90 (s, 9H), 2.21 (ddd, J=9.7, 6.6, 1.6 Hz, 1H), 2.25 (d, J=4.2 Hz, 1H), 2.59 (t, J=6.4 Hz, 2H), 3.50 (t, J=5.6 Hz, 2H), 3.70 (t, J=6.4 Hz, 2H), 3.70 (s, 3H), 3.90–4.04 (m, 1H), 4.08 (dd, J=6.2, 1.6 Hz, 1H), 4.16–4.30 (m, 1H);

IR(neat) cm$^{-1}$; 3459, 2929, 2855, 2229, 1745, 1472, 1463, 1451, 1406, 1361, 1337, 1252, 1177, 1110, 1068, 1006, 927, 898, 836, 777, 669.

(3) Following the substantially same manner as in Example 1(4) using 4-oxa-16,17,18,19,20-pentanor-15-cyclohexyl-13,14-didehydro-PGF$_1$α methyl ester 11,15-bis(tert-butyldimethylsilyl ether) obtained in the above (2), thereby 4-oxa-9-deoxy-9β-chloro-16,17,18,19,20-pentanor-15-cyclohexyl-13,14-didehydro-PGF$_1$α methyl ester 11,15-bis(tert-butyldimethylsilyl ether) was obtained.

$^1$H-NMR(CDCl$_3$, 200 MHz) δ ppm; 0.07 (s, 3H), 0.08 (s, 6H), 0.10 (s, 3H), 0.80–2.20 (m, 18H), 0.88 (s, 9H), 0.90 (s, 9H), 2.29 (ddd, J=8.8, 4.8, 1.8 Hz, 1H), 2.59 (t, J=6.5 Hz, 2H), 3.46 (t, J=5.9 Hz, 2H), 3.70 (t, J=6.5 Hz, 2H), 3.70 (s, 3H), 3.88–4.03 (m, 1H), 4.07 (dd, J=6.3, 1.8 Hz, 1H), 4.20–4.31 (m, 1H);

IR(neat) cm$^{-1}$; 2951, 2929, 2856, 2229, 1745, 1472, 1463, 1451, 1438, 1361, 1252, 1195, 1176, 1109, 1072, 1006, 962, 939, 898, 836, 814, 777, 669.

(4) Following the substantially same manner as in Example 1(5) using the compound obtained in the above (3), thereby the title compound was obtained.

$^1$H-NMR(CDCl$_3$, 300 MHz) δ ppm; 0.84–1.91 (m, 15H), 2.04–2.37 (m, 4H), 2.08 (d, J=5.8 Hz, 1H), 2.10 (d, J=3.6 Hz, 1H), 2.59 (t, J=6.4 Hz, 2H), 3.48 (dt, J=2.0, 6.2 Hz, 2H), 3.70 (t, J=6.4 Hz, 2H), 3.70 (s, 3H), 3.91–4.01 (m, 1H), 4.16 (dt, J=1.8, 5.8 Hz, 1H), 4.32–4.42 (m, 1H);

IR(neat) cm$^{-1}$; 3400, 2927, 2853, 2229, 1739, 1439, 1370, 1331, 1262, 1198, 1178, 1115, 1072, 1017, 893, 847, 757.

EXAMPLE 4

4-Oxa-9-deoxy-9β-chloro-16,17,18,19,20-pentanor-15-cyclohexyl-13,14-didehydro-PGF$_1$α (Compound 52)

To an aqueous suspension (44 ml) of lipase PS (2.27 g) were added an acetone solution (4.34 ml) of the compound obtained in Example 3(81 mg) and phosphate buffer solution (pH=7.0, 0.2 M, 2.2 ml), followed by stirring at 30° C. overnight. The reaction solution was filtered, and the filtrate was made acidic with 1 M hydrochloric acid, salted out with ammonium sulfate and extracted with ethyl acetate. The organic layer was washed with a saturated aqueous sodium chloride solution, dried over anhydrous magnesium sulfate and filtered. The filtrate was concentrated under reduced pressure, and the resulting crude product was purified by a silica gel column chromatography (developing solvent; ethyl acetate) to give the title compound (75 mg).

$^1$H-NMR(CDCl$_3$, 300 MHz) δ ppm; 0.80–1.91 (m, 18H), 2.13–2.36 (m, 4H), 2.59 (t, J=6.0 Hz, 2H), 3.44–3.61 (m, 2H), 3.72 (t, J=6.0 Hz, 2H), 3.92–4.01 (m, 1H), 4.19 (dd, J=6.1, 1.9 Hz, 1H), 4.31–4.41 (m, 1H);

IR(neat) cm$^{-1}$; 3367, 2928, 2854, 2235, 1717, 1450, 1261, 1196, 1114, 1009, 893, 832, 756, 688.

EXAMPLE 5

4-Thia-9-deoxy-9β-chloro-16,17,18,19,20-pentanor-15-cyclohexyl-13,14-didehydro-PGF$_1$α ethyl ester (Compound 5)

(1) Following the substantially same manner as in Example 3(1) using ethyl 4-thia-6-iodohexanoate in place of methyl 4-oxa-6-iodohexanoate in Example 3(1), thereby 4-thia-16,17,18,19,20-pentanor-15-cyclohexyl-13,14-didehydro-PGE$_1$ ethyl ester 11,15-bis(tert-butyldimethylsilyl ether) was obtained.

$^1$H-NMR(CDCl$_3$, 200 MHz) δ ppm; 0.08 (s, 3H), 0.09 (s, 3H), 0.10 (s, 3H), 0.12 (s, 3H), 0.78–1.96 (m, 15H), 0.89 (s, 9H), 0.90 (s, 9H), 1.27 (t, J=7.1 Hz, 3H), 2.08–2.36 (m, 1H), 2.17 (dd, J=18.3, 6.9 Hz, 1H), 2.48–2.93 (m, 8H), 4.05–4.36 (m, 2H), 4.16 (q, J=7.1 Hz, 2H);

IR(neat) cm$^{-1}$: 2929, 2855, 1745, 1472, 1463, 1450, 1407, 1372, 1342, 1250, 1100, 1072, 1006, 939, 898, 884, 838, 778, 669, 586, 428.

(2) Following the substantially same manner as in Example 1(3) using the compound obtained in the above (1), thereby the compounds described below were obtained.

4-Thia-16,17,18,19,20-pentanor-15-cyclohexyl-13,14-didehydro-PGF$_1$α ethyl ester 11,15-bis(tert-butyldimethylsilyl ether)

$^1$H-NMR(CDCl$_3$, 200 MHz) δ ppm; 0.08 (s, 3H), 0.09 (s, 3H), 0.10 (s, 3H), 0.11 (s, 3H), 0.81–2.09 (m, 19H), 0.89 (s, 9H), 0.90 (s, 9H), 1.27 (t, J=7.1 Hz, 3H), 2.32–2.92 (m, 7H), 4.04–4.23 (m, 1H), 4.08 (dd, J=6.4, 2.0 Hz, 1H), 4.16 (q, J=7.1 Hz, 2H), 4.25–4.33 (m, 1H);

IR(neat) cm$^{-1}$: 3462, 2928, 2854, 1736, 1701, 1450, 1371, 1249, 1100, 898, 836, 776.

4-Thia-16,17,18,19,20-pentanor-15-cyclohexyl-13,14-didehydro-PGF$_1$β ethyl ester 11,15-bis(tert-butyldimethylsilyl ether)

$^1$H-NMR(CDCl$_3$, 200 MHz) δ ppm; 0.07 (s, 3H), 0.08 (s, 6H), 0.11 (s, 3H), 0.82–1.98 (m, 19H), 0.88 (s, 9H), 0.90 (s, 9H), 1.27 (t, J=7.1 Hz, 3H), 2.17–2.86 (m, 5H), 2.60 (t, J=6.8 Hz, 2H), 3.93–4.28 (m, 2H), 4.08 (dd, J=6.4, 1.8 Hz, 1), 4.16 (q, J=7.1 Hz, 2H);

IR(neat): 3458, 2929, 2854, 1739, 1639, 1472, 1371, 1342, 1250, 1065, 898, 837, 777, 670.

(3) Following the substantially same manner as in Example 1(4) using 4-thia-16,17,18,19,20-pentanor-15-cyclohexyl-13,14-didehydro-PGF$_1$α ethyl ester 11,15-bis(tert-butyldimethylsilyl ether) obtained in the above (2), thereby 4-thia-9-deoxy-9β-chloro-16,17,18,19,20-pentanor-15-cyclohexyl-13,14-didehydro-PGF$_1$α ethyl ester 11,15-bis(tert-butyldimethylsilyl ether) was obtained.

$^1$H-NMR(CDCl$_3$, 300 MHz) δ ppm; 0.07 (s, 3H), 0.08 (s, 6H), 0.09 (s, 3H), 0.82–1.90 (m, 16H), 0.88 (s, 9H), 0.90 (s, 9H), 1.27 (t, J=7.2 Hz, 3H), 2.05–2.18 (m, 2H), 2.29 (ddd, J=9.0, 4.8, 1.8 Hz, 1H), 2.52–2.64 (m, 4H), 2.74–2.83 (m, 2H), 3.90–4.01 (m, 1H), 4.08 (dd, J=6.2, 1.6 Hz, 1H), 4.16 (q, J=7.2 Hz, 2H), 4.21–4.28 (m, 1H);

IR(neat) cm$^{-1}$: 2929, 2855, 2229, 1739, 1471, 1371, 1342, 1251, 1138, 1099, 1068, 1006, 959, 898, 836, 777, 668.

(4) Following the substantially same manner as in Example 1(5) using the compound obtained in the above (3), thereby the title compound was obtained.

$^1$H-NMR(CDCl$_3$, 300 MHz) δ ppm; 0.95–1.91 (m, 16H), 1.27 (t, J=7.2 Hz, 3H), 2.09–2.36 (m, 4H), 2.32 (ddd, J=9.9, 6.4, 1.9 Hz, 1H), 2.50–2.67 (m, 4H), 2.75–2.84 (m, 2H), 3.88–4.01 (m, 1H), 4.07–4.23 (m, 1H), 4.16 (q, J=7.2 Hz, 2H), 4.31–4.42 (m, 1H);

IR(neat): 3400, 2927, 2852, 2229, 1734, 1449, 1372, 1342, 1297, 1247, 1183, 1149, 1085, 1014, 892, 763, 685.

EXAMPLE 6

4-Thia-9-deoxy-9β-chloro-16,17,18,19,20-pentanor-15-cyclohexyl-13,14-didehydro-PGF$_1$α (Compound 16)

Following the substantially same manner as in Example 4 using the compound obtained in Example 5, thereby the title compound was obtained.

$^1$H-NMR(CDCl$_3$, 300 MHz) δ ppm; 0.84–1.92 (m, 16H), 2.09–3.00 (m, 12H), 3.89–4.01 (m, 1H), 4.19 (dd, J=6.1, 1.9 Hz, 1H), 4.31–4.43 (m, 1H);

IR(neat) cm$^{-1}$: 3367, 2927, 2853, 2235, 1712, 1449, 1415, 1334, 1260, 1188, 1149, 1084, 1008, 948, 895, 802, 758.

EXAMPLE 7

6-Thia-9-deoxy-9β-chloro-16,17,18,19,20-pentanor-15-cyclohexyl-PGF$_1$α methyl ester (Compound 102)

(1) (1E,3S)-1-Iodo-3-(tert-butyldimethylsiloxy)-3-cyclohexyl-1-propene (2.66 g) was dissolved in ether (28 ml), tert-butyl lithium (1.7 M, pentane solution, 8.24 ml) was added at –78° C. After stirring at the same temperature for an hour, lithium 2-thienylcyanocuprate (0.25 M, tetrahydrofuran solution, 39.2 ml) was added, followed by stirring at the same temperature for 20 minutes, and (4R)-2-(N,N-diethylamino)methyl-4-(tert-butyldimethylsiloxy)cyclopent-2-en-1-one (0.25 M, ether solution, 28 ml) was added. The temperature was raised to 0° C. with stirring over 1.5 hours. To the reaction solution were added hexane (70 ml) and a saturated aqueous ammonium chloride solution (105 ml) and, after extraction with hexane, the extract was washed with a saturated aqueous sodium chloride solution, dried, concentrated and purified by a silica gel column chromatography (developing solvent; n-hexane:ethyl acetate=30:1) to give (3R, 4R)-2-methylene-3-[(1E,3S)-3-(tert-butyldimethylsiloxy)-3-cyclohexyl-1-propenyl]-4-(tert-butyldimethylsiloxy)cyclopentan-1-one (910 mg).

$^1$H-NMR(CDCl$_3$, 200 MHz) δ ppm 0.00 (s, 3H), 0.01 (s, 3H), 0.04 (s, 3H), 0.07 (s, 3H), 0.73–1.89 (m, 11 H), 0.88 (s, 9H), 0.90 (s, 9H), 2.33 (dd, J=17.9, 6.3 Hz, 1H), 2.65 (dd, J=17.9, 6.3 Hz, 1H), 3.27–3.91 (m, 2H), 4.07–4.20 (m, 1H), 5.25 (dd, J=2.5, 1.0 Hz, 1H), 5.47 (ddd, J=15.9, 7.2, 0.8 Hz, 1H), 5.61 (dd, J=15.5, 5.1 Hz, 1H), 6.12 (dd, J=2.9, 1.0 Hz, 1H);

IR(neat) cm$^{-1}$; 2954, 2929, 2856, 1734, 1642, 1472, 1451, 1388, 1361, 1253, 1113, 1071, 1006, 973, 943, 923, 900, 837, 776, 690.

(2) Following the substantially same manner as in Example 1(2) using the compound obtained in the above (1) in place of (3R, 4R)-2-methylene-3-[(3S)-3-(tert-butyldimethylsiloxy)-3-cyclohexylprop-1-ynyl]-4-(tert-butyldimethylsiloxy)cyclopentan-1-one in Example 1(2), thereby 6-thia-16,17,18,19,20-pentanor-15-cyclohexyl-PGE$_1$ methyl ester 11,15-bis(tert-butyldimethylsilyl ether) was obtained.

$^1$H-NMR(CDCl$_3$, 200 MHz) δ ppm; –0.01 (s, 3H), 0.04 (s, 3H), 0.06 (s, 3H), 0.07 (s, 3H), 0.70–1.86 (m, 15H), 0.88 (s, 9H), 0.90 (s, 9H), 2.12–2.94 (m, 4H), 2.32 (t, J=7.1 Hz, 2H), 2.51 (t, J=6.9 Hz, 2H), 2.72 (dd, J=13.1, 4.7 Hz, 1H), 2.87 (dd, J=13.1, 5.4 Hz, 1H), 3.67 (s, 3H), 3.77–3.90 (m, 1H), 4.02–4.20 (m, 1H), 5.50 (dd, J=15.5, 6.9 Hz, 1H), 5.62 (dd, J=15.5, 5.1 Hz, 1H);

IR(neat) cm$^{-1}$; 2952, 2930, 2855, 1746, 1740, 1472, 1463, 1451, 1407, 1361, 1252, 1202, 1154, 1116, 1072, 1006, 978, 899, 837, 776, 670.

(3) Following the substantially same manner as in Example 1(3) using the compound obtained in the above (2), thereby the compounds described below were obtained.

6-Thia-16,17,18,19,20-pentanor-15-cyclohexyl-PGF$_1$α methyl ester 11,15-bis(tert-butyldimethylsilyl ether)

$^1$H-NMR(CDCl$_3$, 200 MHz) δ ppm; –0.01 (s, 3H), 0.03 (s, 3H), 0.05 (s, 6H), 0.72–2.08 (m, 19H), 0.87 (s, 9H), 0.89 (s, 9H), 2.33 (t, J=7.1 Hz, 2H), 2.42–2.95 (br, 1H), 2.54 (t, J=6.8 Hz, 2H), 2.61 (dd, J=12.4, 5.1 Hz, 1H), 2.80 (dd, J=12.4, 10.1 Hz, 1H), 3.67 (s, 3H), 3.79 (t, J=5.7 Hz, 1H), 3.96–4.09 (m, 1H), 4.18–4.34 (m, 1H), 5.33 (dd, J=15.5, 8.5 Hz, 1H), 5.48 (dd, J=15.5, 5.8 Hz, 1H);

IR(neat) cm$^{-1}$; 3514, 2929, 2855, 1740, 1472, 1463, 1451, 1388, 1361, 1256, 1208, 1174, 1100, 1052, 1005, 973, 922, 900, 836, 776, 668.

6-Thia-16,17,18,19,20-pentanor-15-cyclohexyl-PGF$_1$β methyl ester 11,15-bis(tert-butyldimethylsilyl ether)

$^1$H-NMR(CDCl$_3$, 200 MHz) δ ppm; –0.01 (s, 3H), 0.02 (s, 3H), 0.03 (s, 6H), 0.72–2.16 (m, 19H), 0.86 (s, 9H), 0.90 (e, 9H), 2.25–2.88 (m, 3H), 2.33 (t, J=7.1 Hz, 2H), 2.37 (dd, J=13.2, 10.7 Hz, 1H), 2.81 (dd, J=13.2, 3.8 Hz, 1H), 3.67 (s, 3H), 3.76–3.86 (m, 1H), 3.96–4.28 (m, 2H), 5.33–5.54 (m, 2H);

IR(neat); 3459, 2952, 2929, 2855, 1740, 1472, 1463, 1451, 1361, 1256, 1208, 1174, 1116, 1067, 1006, 973, 923, 899, 836, 776, 670.

(4) Following the substantially same manner as in Example 1(4) using 6-thia-16,17,18,19,20-pentanor-15-cyclohexyl-PGF$_1$α methyl ester 11,15-bis(tert-butyldimethylsilyl ether) obtained in the above (3), thereby 6-thia-9-deoxy-9β-chloro-16,17,18,19,20-pentanor-15-cyclohexyl-PGF$_1$α methyl ester 11,15-bis(tert-butyldimethylsilyl ether) was obtained.

$^1$H-NMR(CDCl$_3$, 200 MHz) δ ppm; −0.01 (s, 3H), 0.03 (s, 9H), 0.78–1.86 (m, 15H), 0.87 (s, 9H), 0.90 (s, 9H), 1.95–2.46 (m, 4H), 2.33 (t, J=7.3 Hz, 2H), 2.53 (t, J=7.0 Hz, 2H), 2.66 (dd, J=13.0, 5.5 Hz, 1H), 2.75 (dd, J=13.0, 5.4 Hz, 1H), 3.67 (s, 3H), 3.74–3.87 (m, 1H), 4.00–4.36 (m, 2H), 5.41 (dd, J=15.4, 7.5 Hz, 1H), 5.53 (dd, J=15.4, 5.3 Hz, 1H);

IR(neat) cm$^{-1}$; 2952, 2929, 2855, 1740, 1472, 1463, 1451, 1436, 1388, 1361, 1256, 1203, 1170, 1100, 1006, 973, 939, 900, 836, 776, 670.

(5) Following the substantially same manner as in Example 1(5) using the compound obtained in the above (4), thereby the title compound was obtained.

$^1$H-NMR(CDCl$_3$, 200 MHz) δ ppm; 0.80–2.46 (m, 21H), 2.34 (t, J=7.0 Hz, 2H), 2.54 (t, J=7.0 Hz, 2H), 2.64 (dd, J=13.3, 5.2 Hz, 1H), 2.77 (dd, J=13.3, 4.7 Hz, 1H), 3.68 (s, 3H), 3.78–3.91 (m, 1H), 4.09–4.36 (m, 2H), 5.51 (dd, J=15.2, 7.4 Hz, 1H), 5.64 (dd, J=15.2, 6.4 Hz, 1H);

IR(KBr) cm$^{-1}$; 3469, 3366, 2925, 2851, 1741, 1715, 1451, 1432, 1350, 1290, 1232, 1169, 1142, 1073, 986, 970, 916, 890, 848, 741, 626, 494.

EXAMPLE 8

6-Thia-9-deoxy-9β-chloro-16,17,18,19,20-pentanor-15-cyclohexyl-PGF$_1$α (Compound 103)

Following the substantially same manner as in Example 2 using the compound obtained in Example 7, thereby the title compound was obtained.

$^1$H-NMR(CDCl$_3$, 200 MHz) δ ppm; 0.80–2.90 (m, 23H), 2.38 (t, J=6.8 Hz, 2H), 3.78–3.94 (m, 1H), 4.06–5.30 (m, 5H), 5.51 (dd, J=15.3, 7.0 Hz, 1H), 5.63 (dd, J=15.3, 6.3 Hz, 1H);

IR(neat) cm$^{-1}$; 3368, 2924, 2853, 1708, 1450, 1413, 1278, 1224, 1083, 973, 892, 844, 757, 666.

EXAMPLE 9

6-Thia-9-deoxy-9β-chloro-16,17,18,19,20-pentanor-15-cyclohexyl-13,14-dihydro-PGF$_1$α methyl ester (Compound 124)

(1) Following the substantially same manner as in Example 7(1) using (3R)-1-iodo-3-(tert-butyldimethylsiloxy)-3-cyclohexylpropane in place of (1E, 3S)-1-iodo-3-(tert-butyldimethylsiloxy)-3-cyclohexyl-1-propene in Example 7(1), thereby (3R, 4R)-2-methylene-3-[(3R)-3-(tert-butyldimethylsiloxy)-3-cyclohexyl-1-propyl]-4-(tert-butyldimethylsiloxy)cyclopentan-1-one was obtained.

$^1$NMR(CDCl$_3$, 200 MHz) δ ppm; 0.02 (s, 3H), 0.03 (s, 3H), 0.06 (s, 3H), 0.08 (s, 3H), 0.55–1.85 (m, 15H), 0.88 (s, 9H), 0.89 (s, 9H), 2.24–2.38 (m, 1H), 2.53–2.72 (m, 1H), 2.62 (dd, J=18.1, 5.9 Hz, 1H), 3.37–3.49 (m, 1H), 4.06–4.17 (m, 1H), 5.27–5.32 (m, 1H), 6.08 (d, J=2.2 Hz, 1H);

IR(neat) cm$^{-1}$; 2954, 2929, 2856, 1734, 1642, 1473, 1463, 1362, 1256, 1089, 1072, 1006, 939, 836, 775, 670.

(2) Following the substantially same manner as in Example 1(2) using the compound obtained in the above (1) in place of (3R, 4R)-2-methylene-3-[(3S)-3-(tert-butyldimethylsiloxy)-3-cyclohexylprop-1-ynyl]-4-(tert-butyldimethylsiloxy)cyclopentan-1-one in Example 1(2), thereby 6-thia-16,17,18,19,20-pentanor-15-cyclohexyl-13,14-dihydro-PGE$_1$ methyl ester 11,15-bis(tert-butyldimethylsilyl ether) was obtained.

$^1$H-NMR(CDCl$_3$, 200 MHz) δ ppm; 0.03 (s, 6H), 0.05 (s, 3H), 0.08 (s, 3H), 0.78–1.88 (m, 21H), 0.88 (s, 9H), 0.89 (s, 9H), 2.21 (dd, J=18.1, 5.4 Hz, 1H), 2.33 (t, J=7.3 Hz, 2H), 2.51 (t, J=7.0 Hz, 2H), 2.59 (ddd, J=18.1, 6.2, 0.6 Hz, 1H), 2.78 (dd, J=12.9, 7.1 Hz, 1H), 2.87 (dd, J=12.9, 4.8 Hz, 1H), 3.32–3.50 (m, 1H), 3.67 (s, 3H), 4.02–4.17 (m, 1H);

IR(neat) cm$^{-1}$; 2930, 2854, 1746, 1740, 1472, 1463, 1451, 1361, 1256, 1202, 1158, 1110, 1072, 1033, 1006, 940, 882, 836, 775, 668.

(3) Following the substantially same manner as in Example 1(3) using the compound obtained in the above (2), thereby the compounds described below were obtained.

6-Thia-16,17,18,19,20-pentanor-15-cyclohexyl-13,14-dihydro-PGF$_1$α methyl ester 11,15-bis(tert-butyldimethylsilyl ether)

$^1$H-NMR(CDCl$_3$, 200 MHz) δ ppm; 0.03 (2s, 6H), 0.08 (s, 6H), 0.72–1.93 (m, 23H), 0.88 (s, 9H), 0.89 (s, 9H), 2.34 (t, J=7.0 Hz, 2H), 2.57 (t, J=6.9 Hz, 2H), 2.63 (dd, J=12.5, 5.1 Hz, 1H), 2.88 (dd, J=12.5, 9.0 Hz, 1H), 2.96–3.12 (br, 1H), 3.32–3.45 (m, 1H), 3.67 (s, 3H), 3.94–4.04 (m, 1H), 4.10–4.30 (m, 1H);

IR(neat) cm$^{-1}$; 3514, 2929, 2855, 1740, 1472, 1463, 1451, 1436, 1387, 1361, 1256, 1202, 1174, 1089, 1072, 1029, 1006, 939, 868, 836, 774, 667.

6-Thia-16,17,18,19,20-pentanor-15-cyclohexyl-13,14-dihydro-PGF$_1$β methyl ester 11,15-bis(tert-butyldimethylsilyl ether)

$^1$H-NMR(CDCl$_3$, 200 MHz) δ ppm; 0.03 (2s, 12H), 0.72–2.08 (m, 24H), 0.87 (s, 9H), 0.89 (s, 9H), 2.34 (t, J=7.1 Hz, 2H), 2.45 (dd, J=12.9, 10.4 Hz, 1H), 2.57 (t, J=7.0 Hz, 2H), 2.82 (dd, J=12.9, 4.4 Hz, 1H), 3.29–3.46 (m, 1H), 3.68 (s, 3H), 3.86–4.00 (m, 1H), 4.12–4.29 (m, 1H);

IR(neat) cm$^{-1}$; 3436, 2929, 2855, 1740, 1472, 1463, 1451, 1361, 1256, 1208, 1174, 1083, 1072, 1006, 880, 835, 774, 668.

(4) Following the substantially same manner as in Example 1(4) using 6-thia-16,17,18,19,20-pentanor-15-cyclohexyl-13,14-dihydro-PGF$_1$α methyl ester 11,15-bis (tert-butyldimethylsilyl ether) obtained in the above (3), thereby 6-thia-9-deoxy-9β-chloro-16,17,18,19,20-pentanor-15-cyclohexyl-13,14-dihydro-PGF$_1$α methyl ester 11,15-bis (tert-butyldimethylsilyl ether) was obtained.

$^1$H-NMR(CDCl$_3$, 200 MHz) δ ppm; 0.03 (s, 6H), 0.04 (s, 3H), 0.05 (s, 3H), 0.70–2.82 (m, 23H), 0.87 (s, 9H), 0.89 (s, 9H), 2.34 (t, J=7.1 Hz, 2H), 2.54 (t, J=7.0 Hz, 2H), 2.66 (dd, J=13.0, 6.6 Hz, 1H), 2.75 (dd, J=13.0, 6.6 Hz, 1H), 3.33–3.46 (m, 1H), 3.68 (s, 3H), 3.92–4.30 (m, 2H);

IR(neat) cm$^{-1}$; 2929, 2855, 1741, 1472, 1463, 1451, 1386, 1361, 1256, 1202, 1170, 1088, 1072, 1006, 939, 899, 836, 812, 774, 669.

(5) Following the substantially same manner as in Example 1(5) using the compound obtained in the above (4), thereby the title compound was obtained.

$^1$H-NMR(CDCl$_3$, 200 MHz) δ ppm; 0.80–2.90 (m, 25H), 2.35 (t, J=7.0 Hz, 2H), 2.57 (t, J=7.0 Hz, 2H), 2.71 (dd, J=13.1, 5.9 Hz, 1H), 2.80 (dd, J=13.1, 5.3 Hz, 1H), 3.25–3.55 (m, 1H), 3.68 (s, 3H), 4.00–4.38 (m, 2H);

IR(neat) cm$^{-1}$; 3400, 2924, 2853, 1740, 1450, 1418, 1348, 1273, 1208, 1175, 1088, 1063, 996, 892, 844, 503.

EXAMPLE 10

6-Thia-9-deoxy-9β-chloro-16,17,18,19,20-pentanor-15-cyclohexyl-13,14-dihydro-PGF$_1$α (Compound 127)

Following the substantially same manner as in Example 2 using the compound obtained in Example 9, thereby the title compound was obtained.

¹H-NMR(CDCl₃, 200 MHz) δ ppm; 0.78–2.88 (m, 27H), 2.39 (t, J=6.8 Hz, 2H), 3.20–4.80 (br, 3H), 3.35–3.53 (m, 1H), 4.05–4.36 (m, 2H);

IR(neat) cm⁻¹; 3368, 2924, 2853, 1708, 1450, 1418, 1278, 1224, 1088, 1063, 975, 893, 758, 667.

EXAMPLE 11

3-Oxa-6-thia-9-deoxy-9β-chloro-16,17,18,19,20-pentanor-15-cyclohexyl-13,14-didehydro-PGF₁α methyl ester (Compound 84)

(1) Following the substantially same manner as in Example 1(2) using methyl 5-mercapto-3-oxapentanoate in place of methyl 5-mercaptopentanoate in Example 1(2), thereby 3-oxa-6-thia-16,17,18,19,20-pentanor-15-cyclohexyl-13,14-didehydro-PGE₁ methyl ester 11,15-bis(tert-butyldimethylsilyl ether) was obtained.

¹H-NMR(CDCl₃, 200 MHz) δ ppm; 0.08 (s, 3H), 0.09 (s, 3H), 0.10 (s, 3H), 0.13 (s, 3H), 0.82–1.92 (m, 11 H), 0.89 (s, 9H), 0.90 (s, 9H), 2.22 (dd, J=18.0, 6.4 Hz, 1H), 2.40–2.82 (m, 2H), 2.77 (t, J=6.7 Hz, 2H), 2.92 (d, J=5.9 Hz, 2H), 3.09–3.20 (m, 1H), 3.71 (t, J=6.7 Hz, 2H), 3.76 (s, 3H), 4.08 (dd, J=6.2, 1.8 Hz, 1H), 4.13 (s, 2H), 4.28–4.42 (m, 1H);

IR(neat) cm⁻¹; 2930, 2855, 2236, 1752, 1472, 1464, 1451, 1390, 1362, 1252, 1208, 1138, 1066, 1006, 940, 898, 837, 779, 670, 579.

(2) Following the substantially same manner as in Example 1(3) using the compound obtained in the above (1), thereby the compounds described below were obtained.

3-Oxa-6-thia-16,17,18,19,20-pentanor-15-cyclohexyl-13,14-didehydro-PGF₁α methyl ester 11,15-bis,(tert-butyldimethylsilyl ether)

¹H-NMR(CDCl₃, 200 MHz) δ ppm; 0.08 (s, 3H), 0.09 (s, 3H), 0.10 (s, 6H), 0.83–2.22 (m, 15H), 0.88 (s, 9H), 0.90 (s, 9H), 2.50–2.64 (m, 1H), 2.72–2.96 (m, 4H), 3.74 (t, J=6.6 Hz, 2H), 3.76 (s, 3H), 4.07 (dd, J=6.4, 1.8 Hz, 1H), 4.14 (s, 2H), 4.18–4.33 (m, 2H);

IR(neat) cm⁻¹; 3514, 2929, 2855, 2235, 1758, 1472, 1464, 1451, 1388, 1362, 1251, 1214, 1138, 1100, 1062, 1006, 927, 898, 837, 777, 668.

3-oxa-6-thia-16,17,18,19,20-pentanor-15-cyclohexyl-13,14-didehydro-PGF₁β methyl ester 11,15-bis(tert-butyldimethylsilyl ether)

¹H-NMR(CDCl₃, 200 MHz) δ ppm; 0.07 (s, 3H), 0.08 (s, 6H), 0.11 (s, 3H), 0.83–2.09 (m, 15H). 0.88 (s, 9H), 0.90 (s, 9H), 2.35 (ddd, J=10.0, 6.3, 1.8 Hz, 1H), 2.46–3.12 (m, 4H), 3.67–3.81 (m, 2H), 3.76 (s, 3H), 4.05–4.30 (m, 2H), 4.08 (dd, J=6.3, 1.6 Hz, 1H), 4.13 (s, 2H);

IR(neat) cm⁻¹; 3469, 2952, 2929, 2855, 2236, 1758, 1472, 1463, 1451, 1389, 1361, 1252, 1214, 1138, 1066, 1006, 927, 898, 837, 777, 669.

(3) Following the substantially same manner as in Example 1(4) using 3-oxa-6-thia-16,17,18,19,20-pentanor-15-cyclohexyl-13,14-didehydro-PGF₁α methyl ester 11,15-bis(tert-butyldimethylsilyl ether) obtained in the above (2) under an argon stream, thereby 3-oxa-6-thia-9-deoxy-9β-chloro-16,17,18,19,20-pentanor-15-cyclohexyl-13,14-didehydro-PGF₁α methyl ester 11,15-bis(tert-butyldimethylsilyl ether) was obtained.

¹H-NMR(CDCl₃, 200 MHz) δ ppm; 0.07 (s, 3H), 0.08 (s, 3H), 0.09 (s, 3H), 0.11 (s, 3H), 0.82–1.92 (m, 11H), 0.88 (s, 9H), 0.90 (s, 9H), 2.13–2.42 (m, 3H), 2.57 (ddd, J=9.1, 5.3, 1.8 Hz, 1H), 2.81 (t, J=6.7 Hz, 2H), 2.88 (dd, J=5.4, 0.8 Hz, 2H), 3.74 (t, J=6.7 Hz, 2H), 3.77 (s, 3H), 4.05–4.34 (m, 2H), 4.08 (dd, J=6.2, 1.8 Hz, 1H), 4.14 (s, 2H);

IR(neat) cm⁻¹; 2952, 2929, 2855, 2236, 1758, 1746, 1472, 1464, 1451, 1389, 1362, 1252, 1208, 1138, 1100, 1006, 939, 898, 837, 777, 669.

(4) Following the substantially same manner as in Example 1(5) using the compound obtained in the above (3), thereby the title compound was obtained.

¹H-NMR(CDCl₃, 200 MHz) δ ppm; 0.92–2.00 (m, 13H), 2.22–2.48 (m, 3H), 2.65 (ddd, J=10.0, 6.4, 1.9 Hz, 1H), 2.83 (t, J=6.6 Hz, 2H), 2.92 (d, J=5.1 Hz, 2H), 3.75 (t, J=6.6 Hz, 2H), 3.77 (p, 3H), 4.10–4.29 (m, 2H), 4.15 (s, 2H), 4.33–4.46 (m, 1H);

IR(neat) cm⁻¹; 3400, 2925, 2853, 2236, 1752, 1746, 1440, 1288, 1218, 1138, 1083, 1011, 955, 893, 834, 704, 579.

EXAMPLE 12

3-Oxa-6-thia-9β-chloro-13,14-didehydro-16,17,18,19,20-pentanor-15-cyclohexyl-9-deoxy-PGF₁α (Compound 97)

Following the substantially same manner as in Example 2 using the compound obtained in Example 11, thereby the title compound was obtained.

¹H-NMR(CDCl₃, 200 MHz) δ ppm; 0.92–1.94 (m, 11H), 2.16–2.48 (m, 3H), 2.64 (ddd, J=10.1, 6.8, 1.8 Hz, 1H), 2.72–3.07 (m, 2H), 2.83 (t, J=6.4 Hz, 2H), 3.77 (t, J=6.4 Hz, 2H), 3.92–4.64 (m, 6H), 4.17 (s, 2H);

IR(neat) cm⁻¹; 3368, 2924, 2854, 2236, 1734, 1450, 1429, 1348, 1278, 1230, 1132, 1083, 1008, 954, 893, 834, 758, 676, 578.

EXAMPLE 13

3,6-Dithia-9-deoxy-9β-chloro-16,17,18,19,20-pentanor-15-cyclohexyl-13,14-didehydro-PGF₁α methyl ester (Compound 77)

(1) Following the substantially same manner as in Example 1(2) using methyl 5-mercapto-3-thiapentanoate in place of methyl 5-mercaptopentanoate in Example 1(2), thereby 3,6-dithia-16,17,18,19,20-pentanor-15-cyclohexyl-13,14-didehydro-PGE₁ methyl ester 11,15-bis(tert-butyldimethylsilyl ether) was obtained.

¹H-NMR(CDCl₃, 200 MHz) δ ppm; 0.08 (s, 3H), 0.09 (s, 3H), 0.10 (s, 3H), 0.13 (s, 3H), 0.84–1.93 (m, 11H), 0.89 (s, 9H), 0.90 (s, 9H), 2.22 (dd, J=18.0, 6.4 Hz, 1H), 2.41–2.55 (m, 1H), 2.64–2.96 (m, 7H), 3.07–3.18 (m, 1H), 3.27 (s, 2H), 3.75 (s, 3H), 4.09 (dd, J=6.4, 1.5 Hz, 1H), 4.29–4.41 (m, 1H);

IR(neat) cm⁻¹; 2929, 2855, 2236, 1746, 1472, 1464, 1436, 1407, 1390, 1362, 1257, 1121, 1065, 1006, 940, 898, 837, 778, 670.

(2) Following the substantially same manner as in Example 1(3) using the compound obtained in the above (1), thereby the compounds described below were obtained.

3,6-Dithia-16,17,18,19,20-pentanor-15-cyclohexyl-13,14-didehydro-PGF₁α methyl ester 11,15-bis, (tert-butyldimethylsilyl ether)

¹H-NMR(CDCl₃, 200 MHz) δ ppm; 0.08 (s, 3H), 0.09 (s, 3H), 0.10 (s, 6H), 0.84–2.20 (m, 15H), 0.89 (s, 9H), 0.90 (s, 9H), 2.50–2.64 (m, 1H), 2.73–2.96 (m, 6H), 3.27 (s, 2H), 3.75 (s, 3H), 4.08 (dd, J=6.2, 1.8 Hz, 1H), 4.20–4.33 (m, 2H);

IR(neat) cm$^{-1}$; 3436, 2929, 2855, 2236, 1740, 1472, 1463, 1436, 1387, 1362, 1256, 1100, 1062, 1006, 898, 836, 777, 670.

3,6-Dithia-16,17,18,19,20-pentanor-15-cyclohexyl-13,14-didehydro-PGF$_1\beta$ methyl ester 11,15-bis(tert-butyldimethylsilyl ether)

$^1$H-NMR (CDCl$_3$, 200 MHz) δ rpm; 10, 0.07 (s, 3 H), 0.08 (s, 6H), 0.11 (s, 3H), 0.83–2.07 (m, 15H), 0.88 (s, 9H), 0.90 (s, 9H), 2.36 (ddd, J=10.0, 6.4, 1.5 Hz, 1H), 2.49–3.06 (m, 4H), 2.56 (dd, J=13.2, 9.4 Hz, 1H), 3.00 (dd, J=13.2, 4.3 Hz, 1H), 3.27 (s, 2H), 3.75 (s, 3H), 4.04–4.31 (m, 3H);

IR(neat) cm$^{-1}$; 3468, 2929, 2855, 2236, 1740, 1472, 1464, 1436, 1388, 1362, 1338, 1279, 1252, 1100, 1066, 1006, 898, 836, 777, 670.

(3) Following the substantially same manner as in Example 1(4) using 3,6-dithia-16,17,18,19,20-pentanor-15-cyclohexyl-13,14-didehydro-PGF$_1\alpha$ methyl ester 11,15-bis(tert-butyldimethylsilyl ether) obtained in the above (2), thereby 3,6-dithia-9-deoxy-9β-chloro-16,17,18,19,20-pentanor-15-cyclohexyl-13,14-didehydro-PGF$_1\alpha$ methyl ester 11,15-bis(tert-butyldimethylsilyl ether) was obtained.

$^1$H-NMR(CDCl$_3$, 200 MHz) δ ppm; 0.08 (s, 6H), 0.09 (s, 3H), 0.11 (s, 3H), 0.80–1.92 (m, 11H), 0.88 (s, 9H), 0.90 (s, 9H), 2.14–2.39 (m, 3H), 2.57 (ddd, J=9.1, 5.0, 1.6 Hz, 1H), 2.74–2.96 (m, 6H), 3.27 (s, 2H), 3.75 (t, J=6.7 Hz, 2H), 4.05–4.34 (m, 2H), 4.09 (dd, J=6.3, 1.6 Hz, 1H);

IR(neat) cm$^{-1}$; 2929, 2855, 2236, 1740, 1472, 1464, 1436, 1389, 1362, 1278, 1257, 1100, 1006, 962, 927, 898, 836, 778, 669, 588.

(4) Following the substantially same manner as in Example 1(5) using the compound obtained in the above (3), thereby the title compound was obtained.

$^1$H-NMR(CDCl$_3$, 200 MHz) δ ppm; 0.98–2.02 (m, 13H), 2.22–2.47 (m, 3H), 2.62 (ddd, J=10.1, 6.4, 1.8 Hz, 1H), 2.75–2.99 (m, 6H), 3.28 (s, 2H), 3.76 (s, 3H), 4.10 (m, 2H), 4.06–4.27 (m, 2H), 4.32–4.47 (m, 1H);

IR(neat) cm$^{-1}$; 3400, 2925, 2852, 2236, 1734, 1730, 1436, 1284, 1203, 1142, 1083, 1008, 893, 833, 773, 692, 578.

EXAMPLE 14

3,6-Dithia-9-deoxy-9α-chloro-16,17,18,19,20-pentanor-15-cyclohexyl-13,14-didehydro-PGF$_1\beta$ methyl ester (Compound 193)

(1) Following the substantially same manner as in Example 1(4) using 3,6-dithia-16,17,18,19,20-pentanor-15-cyclohexyl-13,14-didehydro-PGF$_1\beta$ methyl ester 11,15-bis(tert-butyldimethylsilyl ether) obtained in Example 13(2), thereby 3,6-dithia-9-deoxy-9α-chloro-16,17,18,19,20-pentanor-15-cyclohexyl-13,14-didehydro-PGF$_1\beta$ methyl ester 11,15-bis(tert-butyldimethylsilyl ether) was obtained, followed by carrying out the substantially same manner as in Example 1(5) to give the title compound.

$^1$H-NMR(CDCl$_3$, 200 MHz) δ ppm; 0.87–2.34 (m, 15H), 2.57–3.00 (m, 8H), 3.28 (s, 2H), 3.75 (s, 3H), 4.12–4.40 (m, 2H), 4.53–4.63 (m, 1H);

IR(neat) cm$^{-1}$; 3460, 2924, 2851, 2236, 1734, 1436, 1283, 1141, 1082, 1009, 893, 837, 689.

EXAMPLE 15

3,6-Dithia-9-deoxy-9β-chloro-16,17,18,19,20-pentanor-15-cyclohexyl-13,14-didehydro-PGF$_1\alpha$ (Compound 89)

Following the substantially same manner as in Example 2 using the compound obtained in Example 13, thereby the title compound was obtained.

$^1$H-NMR(CDCl$_3$, 200 MHz) δ ppm; 0.92–2.00 (m, 11H), 2.15–3.12 (m, 10H), 3.23 (d, J=14.2 Hz, 1H), 3.32 (d, J=14.2 Hz, 1H), 3.57–4.03 (br, 3H), 4.06–4.28 (m, 1H), 4.24 (dd, J=6.2, 2.0 Hz, 1H), 4.34–4.49 (m, 1H);

IR(neat) cm$^{-1}$; 3368, 2925, 2853, 2236, 1718, 1450, 1424, 1278, 1206, 1149, 1082, 1005, 957, 921, 893, 876, 833, 758, 670, 578.

Experiment [Measurement of cAMP production promoting action in EBTr [NBL-4] cell derived from bovine embryonic trachea]

According to the method of Ito et al. in *Br. J. Pharmacol.*, vol. 99, page 13–14 (1990), the following test was carried out.

That is, EBTr [NBL-4] cells derived from bovine embryonic trachea (produced by Dainippon Pharmaceutical Co.) were inoculated on 24-well plates (6×10$^4$ cells/well) (manufactured by Sumitomo Bakelite Co.), and cultured on a growth medium (MEM Earle's medium including 10% calf serum, 2mM glutamine and non-essential amino acids) for 48 hours, followed by cultivation on 0.5 ml of a growth medium including the test compound and 0.5 mM 3-isobutyl-1-methylxanthine) for 15 minutes. After the completion of the reaction, the cells were washed with a phosphate buffer (not including Ca++ and Mg++), 0.6 ml of 65% aqueous ethanol solution was added, followed by allowing to stand at 4° C. for an hour, and the resulting cAMP was extracted. After evaporation of the solvent by a centrifugal evaporator, the amount of cAMP was measured by using a cAMP EIA System (manufactured by Amersham Co.).

When an amount of cAMP obtained by adding PGD$_2$ in a concentration of 10 μM was regarded as 100%, a concentration required to produce 50% of the amount of cAMP was measured as EC$_{50}$.

Results are shown in Table 1.

TABLE 1

| Compound | cAMP production promoting action EC$_{50}$ (nM) |
| --- | --- |
| Compound 19 | 17.3 |
| Compound 97 | 5.13 |
| PGD$_2$ | 124 |

(note) Compounds 19 and 97 are those prepared in the examples as described above. The test compounds were each used as a form of an ethanol solution, and compared with a vehicle-treated group as a control.

It is found from the above results that Compounds 19 and 97 have a strong cAMP production promoting action.

INDUSTRIAL APPLICABILITY

The compounds of the present invention have a PGD$_2$-like agonistic action, therefore they are useful as therapeutic agents of circulatory diseases such as renal diseases, ischemic heart diseases, heart failure or hypertension, and glaucoma.

In addition, the compounds of the present invention have not only a sufficient sleep-inducing action, but also excellent stability and intracerebral transition, therefore they are useful as a drug having a sleep-inducing action.

What is claimed is:

1. A prostaglandin derivative represented by Formula (I):

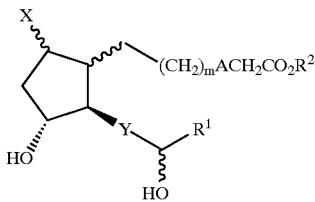

wherein X is a halogen atom in the α- or β-position, Y is an ethylene group, a vinylene group or an ethynylene group, A is a group represented by the formula:

$O(CH_2)_n$, $S(O)_p(CH_2)_n$, $O(CH_2)_qO(CH_2)_r$, $O(CH_2)_qS(O)_p(CH_2)_r$, $S(O)_p(CH_2)_qS(O)_p(CH_2)_r$ or $S(O)_p(CH_2)_qO(CH_2)_r$ (wherein n is an integer of 1 to 5, p is 0, 1 or 2, q is an integer of 1 to 3, and r is 0 or 1), $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a $C_{5-10}$ alkyl group, a $C_{5-10}$ alkenyl group, a $C_{5-10}$ alkynyl group or a bridged cyclic hydrocarbon group, $R^2$ is a hydrogen atom, a $C_{1-10}$ to alkyl group or a $C_{3-10}$ cycloalkyl group, and m is 0, 1 or 2], a pharmaceutically acceptable salt thereof or a hydrate thereof.

2. The prostaglandin derivative of Formula (I) according to claim 1 wherein $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a branched $C_{5-10}$ alkyl group, a branched $C_{5-10}$ alkenyl group, a branched $C_{5-10}$ alkynyl group or a bridged cyclic hydrocarbon group; the pharmaceutically acceptable salt thereof or the hydrate thereof.

3. The prostaglandin derivative of Formula (I) according to claim 2 wherein X is a chlorine or bromine atom in the α- or β-position, $R^1$ is a $C_{3-10}$ cycloalkyl group, a $C_{3-10}$ cycloalkyl-$C_{1-4}$ alkyl group or a branched $C_{5-10}$ alkenyl group, and $R^2$ is a hydrogen atom or a $C_{1-10}$ alkyl group; the pharmaceutically acceptable salt thereof or the hydrate thereof.

4. The prostaglandin derivative of Formula (I) according to claim 1 wherein is Y is a vinylene group; the pharmaceutically acceptable salt thereof or the hydrate thereof.

5. The prostaglandin derivative of Formula (I) according to claim 1 wherein is Y is an ethynylene group; the pharmaceutically acceptable salt thereof or the hydrate thereof.

6. The prostaglandin derivative of Formula (I) according to claim 1 wherein is A is a group represented by the formula:

$S(O)_p(CH_2)_n$, $S(O)_p(CH_2)_qS(O)_p(CH_2)_r$ or $S(O)_p(CH_2)_qO(CH_2)_r$ (wherein n is an integer of 1 to 5, p is 0, 1 or 2, q is an integer of 1 to 3, and r is 0 or 1); the pharmaceutically acceptable salt thereof or the hydrate thereof.

7. The prostaglandin derivative of Formula (I) according to claim 6 wherein is p is 0; the pharmaceutically acceptable salt thereof or the hydrate thereof.

8. A pharmaceutical preparation which comprises as an effective ingredient the prostaglandin derivative according to any one of claims 1 to 7, the pharmaceutically acceptable salt thereof or the hydrate thereof.

* * * * *